(12) United States Patent
Fink et al.

(10) Patent No.: US 8,481,260 B2
(45) Date of Patent: *Jul. 9, 2013

(54) METHODS FOR DIAGNOSING EPISODIC MOVEMENT DISORDERS AND RELATED CONDITIONS

(75) Inventors: John K. Fink, Ann Arbor, MI (US); Shirley Rainier, Sylvania, OH (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/729,773

(22) Filed: Mar. 23, 2010

(65) Prior Publication Data

US 2010/0227330 A1   Sep. 9, 2010

Related U.S. Application Data

(63) Continuation of application No. 11/167,838, filed on Jun. 27, 2005, now Pat. No. 7,727,719.

(60) Provisional application No. 60/583,058, filed on Jun. 25, 2004.

(51) Int. Cl.
*C12Q 1/00* (2006.01)

(52) U.S. Cl.
USPC .......................................................... 435/6.1

(58) Field of Classification Search
None
See application file for complete search history.

(56) References Cited

PUBLICATIONS

Biology pages (retrieved from http://users.rcn.com/jkimball.ma.ultranet/BiologyPages/P/Polypeptides.html on Apr. 17, 2012 1 page).*
Chen et al ('Presence of alanine-to-valine substitutions in myofibrillogenesis regulator 1 in paroxysmal nonkinesigenic dyskinesia' Arch Neurol v62 Apr. 2005 pp. 597-600).*
Shen et al ('Mutations in PNKD causing paroxysmal dyskinesia alters protein cleavage and stability' Human Molecular Genetics v20(12) 2011 pp. 2322-2332).*
Li, et al., Characterization of MR-1, a novel myofibrillogenesis regulator in human muscle, Jun. 22, 2004, Acta Biochimica et Biophysica Sinica, 36(6):412-418.
Muller et al., Clinical and molecular genetics of primary dystonias, 1998, Neurogenetics, 1:165-177.

Web site http://dictionary.reference.com/browse/diagnostic accessed Apr. 30, 2008, 1 page.
Lee, et al., Human Molecular Genetics, 2004 v13 pp. 3161-3170.
Rainier, et al., Arch Neurol, 2004, pp. 1025-1029.
Partridge, et al., Journal of Cereal Science, 2002, v35 pp. 189-200.
Skvortsova, et al. (European Journal of Human Genetics v12 2004 pp. 241-244).
Fink et al., "Paroxysmal dystonic choreoathetosis: tight linkage to chromosome 2q," Am J Hum Genet. 1996, 59:140-145.
Fouad et al., "A gene for familial paroxysmal dyskinesia (FPD1) maps to chromosome 2q.," Am J Hum Genet. 1996, 59:135-139.
Jarman et al., "Paroxysmal dystonic choreoathetosis. Genetic linkage studies in a British family," Brain. 1997, 120:2125-2130.
Matsuo et al., "Familial paroxysmal dystonic choreoathetosis: clinical findings in a large Japanese family and genetic linkage to 2q," Arch Neurol. 1999, 56:721-726.
Hofele et al., "Gene locus FPD1 of the dystonic Mount-Reback type of autosomal-dominant dominant paroxysmal choreoathetosis," Neurology. 1997, 49:1252-1257.
Przuntek et al., "TTherapeutic aspects of kinesiogenic paroxysmal choreoathetosis and familial paroxysmal choreoathetosis of the Mount and Reback type," J Neurol. 1983, 230:163-169.
Raskind et al., "Further localization of a gene for paroxysmal dystonic choreoathetosis to a 5-cM region on chromosome 2q34," Hum Genet. 1998, 102:93-97.
Bohnen et al., "(+)-alpha-[11C]Dihydrotetrabenazine PET imaging in familial paroxysmal dystonic choreoathetosis," Neurology. 1999, 52:1067-1069.
Grunder et al., "Acid-sensing ion channel (ASIC) 4 gene: physical mapping, genomic organisation, and evaluation as a candidate for paroxysmal dystonia," Eur J Hum Genet. 2001, 9:672-676.
Tokarz D., et al., "Mutation analysis of two candidate genes in the paroxysmal dystonic choreoathetosis locus on chromosome 2q," Am J Hum Genet. 2001, 69:629.
Rainier et al., "NIPA1 gene mutations cause autosomal dominant hereditary spastic paraplegia (SPG6)," AmJ Hum Genet. 2003, 73:967-971.
Zhao et al., "Mutations in a newly identified GTPase gene cause autosomal dominant hereditary spastic paraplegia,"Nat Genet. 2001, 29:326-331.
Fink et al., "Paroxysmal dystonic choreoathetosis linked to chromosome 2q: clinical analysis and proposed pathophysiology.," Neurology. 1997, 49:177-183.

* cited by examiner

*Primary Examiner* — Cecilia J Tsang
*Assistant Examiner* — Ronald Niebauer
(74) *Attorney, Agent, or Firm* — Casimir Jones SC

(57) ABSTRACT

The present invention provides compositions and methods for research, diagnostic, drug screening, and therapeutic applications related to paroxysmal dystonic choreoathetosis and related conditions. In particular, the present invention provides mutations in the myofibrillogenesis regulator 1 (MR-1) gene associated with such conditions.

3 Claims, 12 Drawing Sheets

Figure 1.
Wild Type human MR-1 nucleic acid sequence (SEQ ID NO: 1)

```
   1 actattcccg gcggggagcg cggtgaagcg ggggtgggat ctgaacatgg cggcggtggt
  61 agctgctacg gcgctgaaga gccgggggggc gagaaatgcc cgcgtcctcc gggggattct
 121 cgcaggagcc acagctaaca aggtttctca taacaggacc cgggccctgc aaagccacag
 181 ctcctcagag ggcaaggagg aacctgaacc cctatccccg gagctggaat acattcccag
 241 aaagagggc aagaacccca tgaaagctgt gggactggcc tggtacagcc tgtacacccg
 301 caccctggctc gggtacctct tctaccgaca gcagctgcgc agggctcgga atcgctaccc
 361 taaaggccac tcgaaaaccc agccccgcct cttcaatgga gtgaaggtgc ttcccatccc
 421 tgtcctctcg gacaactaca gctacctcat catcgacacc caggcccagc tggctgtggc
 481 tgtggaccct tcagaccctc gggctgtgca ggcttccatt gaaaaggaag gggtcaccttt
 541 ggtcgccatt ctgtgtactc acaagcactg ggaccacagt ggagggaacc gtgacctcag
 601 ccggcggcac cgggactgtc gggtgtacgg gagccctcag gacggcatcc cctacctcac
 661 ccatccctg tgtcatcaag atgtggtcag cgtgggacgg cttcagatcc gggccctggc
 721 tacacctggc cacacacaag gccatctggt ctacctactg gatggggagc cctacaaggg
 781 tccctcctgc ctcttctcag gggacctgct cttcctctct ggctgtgggc ggacctttga
 841 gggcaatgca gagaccatgc tgagctcact ggacactgtg ctggggctag gggatgacac
 901 ccttctgtgg cctggtcatg agtatgcaga ggagaacctg ggctttgcag gtgtggtgga
 961 gcccgagaac ctggcccggg agaggaagat gcagtgggtg cagcggcagc ggctggagcg
1021 caagggcacg tgcccatcta ccctgggaga ggagcgctcc tacaacccgt tcctgagaac
1081 ccactgcctg gcgctacagg aggctctggg gccggggccg ggccccactg gggatgatga
1141 ctactcccgg gcccagctcc tggaagagct ccgccggctg aaggatatgc acaagagcaa
1201 gtgatgcccc cagcgccccc agcccagccc actccccgca tggggaggcc gccaccacca
1261 acacctcatc atccttctca tcgctaacac caccacctcc atcggcaccc aagcgggcat
1321 catccccca cactgctcag gggaggggag ggatcaggcg atgagactgt gaggccaaaa
1381 gaagcgggcc tgttggaggc tgggaacccc gcagcgcgag gctgcctcat caacggcaag
1441 aggaaaggag gggtctcggg acatctccag accctaccaa ctgggagggt cccctcctcc
1501 ttccctactc ctgggacggc agcaaggaca tggggctgc tgttagcttc tccgtcagga
1561 ggcctcactc actgtagccc tggaacccag ggtccatctt gcccttcccc catccatggt
1621 tgggaaagaa gctcagcccc tcacagtggc ctcaagtgtg atgccttaca aaagcaccac
1681 tcagatgggc agctggactc tggtgtcctg agactctgcc ctcttcccac agcctccctg
1741 cccccacccat ccctgcaaag ccattttca gacagaccca ttcctaagaa cactgaaggg
1801 ctggaatgct ggctggccac tctctgcctc agtggcctcc ctacagcctg gaagaaggag
1861 ggtcctgatt gccaaggaaa cctctcctca ttgggctaag agacactgg agtctggagt
1921 gtggagcccc acagtcttgc aggtcacatg ctctccttgc acatctggcc tggttgtacc
1981 cactggcctc tgcctctgcc ctgggccaaa agggcccctc cttgccaggg gagagacagc
2041 cacggtcctc tttggccgat gctgtattct cattttggcc cttgttctta ggcccgtctg
2101 cccgcctttcc tccatctaac ctttcctgtt ttatccgcag cccttttctt ctttgagtta
2161 gtaaagattt attctgtaac ctgacactca tctgcccctt tgcagtttgc cagccatatt
2221 cccatgtgat ttcccactgg atccaggccc ccatccggct ggcaggaggg ggctctgacg
2281 tgcaggttgg aaatcagaag tctgtgagag cgcgggagtg catggcagct ctgggtccca
2341 gacctggccc gacccctctg cttcacctcc agctctgctg ctcctctact cttgggttga
2401 gatccctttg gagccacagc gaggaaccct gtggtcctca ggcaggtgta ccttgagtca
2461 gccagagccc ctcttttcct gtgtcaaagc ctgccctcgg gctctgctca cctctggtga
2521 ccctccaaga tgccctgcc ctcagtttcc cctcatgatc tggcctctgc ccccttctct
2581 agccacagcc tctagtacac tttagcaata ccaccagact agttagagtt ccgcactcac
2641 caagcaagac atacagtttc atgcctctgt gccttcgctc atgctgtttc ttccgactgg
2701 aatgccttcc cctgctcctc ctgccttgtc tgcctggcaa gttcatctct cacgatcccc
2761 tcaaaggccc cctcctcag gaaggcaacc cctgtgcccc tccctccag gctacctctg
2821 cactttgtca atgcttctct tgtggcactt atcacgctgt atttactttg tttacatgtt
2881 tgtctcccct tctagactgt gaatcttaa gggcatggac tgtatcttat gcatctctgt
2941 atttctgcgc ctagcacggt gcctagcaca cagtaggcgc tcaataaatg ttgaatgaat
3001 gaatgattta atcaagaaaa aaaaaaaaa aa
```

Figure 2.

Mutant human MR-1 nucleic acid sequence (C66T) (SEQ ID NO: 2)

```
   1 actattcccg gcggggagcg cggtgaagcg ggggtgggat ctgaacatgg cggcggtggt
  61 agctgttacg gcgctgaaga gccgggggc gagaaatgcc cgcgtcctcc gggggattct
 121 cgcaggagcc acagctaaca aggtttctca taacaggacc cgggccctgc aaagccacag
 181 ctcctcagag ggcaaggagg aacctgaacc cctatccccg gagctggaat acattcccag
 241 aaagagggc aagaacccca tgaaagctgt gggactggcc tggtacagcc tgtacacccg
 301 cacctggctc gggtacctct tctaccgaca gcagctgcgc agggctcgga atcgctaccc
 361 taaaggccac tcgaaaaccc agccccgcct cttcaatgga gtgaaggtgc ttcccatccc
 421 tgtcctctcg gacaactaca gctacctcat catcgacacc caggcccagc tggctgtggc
 481 tgtggaccct tcagaccctc gggctgtgca ggcttccatt gaaaaggaag gggtcacctt
 541 ggtcgccatt ctgtgtactc acaagcactg gaccacagt ggagggaacc gtgacctcag
 601 ccggcggcac cgggactgtc gggtgtacgg gagccctcag gacggcatcc cctacctcac
 661 ccatcccctg tgtcatcaag atgtggtcag cgtgggacgg cttcagatcc gggccctggc
 721 tacacctggc cacacacaag gccatctggt ctacctactg gatggggagc cctacaaggg
 781 tccctcctgc ctcttctcag gggacctgct cttcctctct ggctgtgggc ggacctttga
 841 gggcaatgca gagaccatgc tgagctcact ggacactgtg ctggggctag ggatgacac
 901 ccttctgtgg cctggtcatg agtatgcaga ggagaacctg ggctttgcag gtgtggtgga
 961 gcccgagaac ctggcccggg agaggaagat gcagtgggtg cagcggcagc ggctggagcg
1021 caagggcacg tgcccatcta ccctgggaga ggagcgctcc tacaacccgt tcctgagaac
1081 ccactgcctg gcgctacagg aggctctggg gccggggccg ggcccactg gggatgatga
1141 ctactcccgg gcccagctcc tggaagagct ccgccggctg aaggatatgc acaagagcaa
1201 gtgatgcccc cagcgccccc agcccagccc actccccgca tggggaggcc gccaccacca
1261 acacctcatc atccttctca tcgctaacac caccacctcc atcggcaccc aagcgggcat
1321 catcccccca cactgctcag gggaggggag ggatcaggcg atgagactgt gaggccaaaa
1381 gaagcgggcc tgttggaggc tgggaaccc gcagcgcgag gctgcctcat caacggcaag
1441 aggaaaggag gggtctcggg acatctccag accctaccaa ctgggagggt cccctcctcc
1501 ttccctactc ctgggacggc agcaaggaca tgggggctgc tgttagcttc tccgtcagga
1561 ggcctcactc actgtagccc tggaacccag ggtccatctt gcccttcccc catccatggt
1621 tgggaaagaa gctcagcccc tcacagtggc ctcaagtgtg atgccttaca aaagcaccac
1681 tcagatgggc agctggactc tggtgtcctg agactctgcc ctcttcccac agcctccctg
1741 ccccacccat ccctgcaaag ccatttttca gacagagcca ttcctaagaa cactgaaggg
1801 ctggaatgct ggctggccac tctctgcctc agtgcctcc ctacagcctg gaagaaggag
1861 ggtcctgatt gccaaggaaa cctctcctca ttgggctaag gagacactgg agtctggagt
1921 gtggagcccc acagtcttgc aggtcacatg ctctccttgc acatctggcc tggttgtacc
1981 cactggcctc tgcctctgcc ctgggccaaa agggcccctc cttgccaggg gagagacagc
2041 cacggtcctc tttggccgat gctgtattct cattttggcc cttgttctta ggcccgtctg
2101 cccgccttcc tccatctaac ctttcctgtt ttatccgcag cccttttctt ctttgagtta
2161 gtaaagattt attctgtaac ctgacactca tctgcccctt tgcagtttgc cagccatatt
2221 cccatgtgat ttcccactgg atccaggccc ccatccggct ggcaggaggg ggctctgacg
2281 tgcaggttgg aaatcagaag tctgtgagag cgcgggagtg catggcagct ctgggtccca
2341 gacctggccc gaccectctg cttcacctcc agctctgctg ctcctctact cttgggttga
2401 gatcccttg gagccacagc gaggaaccct gtggtcctca ggcaggtgta ccttgagtca
2461 gccaggagcc ctcttttcct gtgtcaaagc ctgccctcgg gctctgctca cctctggtga
2521 ccctccaaga tgccctgcc ctcagtttcc cctcatgatc tggcctctgc cccttctct
2581 agccacagcc tctagtacac tttagcaata ccaccagact agttagagtt ccgcactcac
2641 caagcaagac atacagtttc atgcctctgt gccttcgctc atgctgtttc ttccgactgg
2701 aatgccttcc cctgctcctc ctgccttgtc tgcctggcaa gttcatctct cacgatcccc
2761 tcaaaggccc cctcctcag gaaggcaacc cctgtgcccc tcccctccag gctacctctg
2821 cactttgtca atgcttctct tgtggcactt atcacgctgt attttacttg tttacatgtt
2881 tgtctcccct tctagactgt gaatccttaa gggcatggac tgtatcttat gcatctctgt
2941 atttctgcgc ctagcacggt gcctagcaca cagtaggcgc tcaataaatg ttgaatgaat
3001 gaatgattta atcaagaaaa aaaaaaaaa aa
```

Figure 3.

Mutant human MR-1 nucleic acid sequence (C72T) (SEQ ID NO: 3)

```
   1 actattcccg gcggggagcg cggtgaagcg ggggtgggat ctgaacatgg cggcggtggt
  61 agctgctacg gtgctgaaga gccgggggc gagaaatgcc cgcgtcctcc ggggattct
 121 cgcaggagcc acagctaaca aggtttctca taacaggacc cgggccctgc aaagccacag
 181 ctcctcagag ggcaaggagg aacctgaacc cctatccccg gagctggaat acattcccag
 241 aaagagggc aagaaccca tgaaagctgt gggactggcc tggtacagcc tgtacacccg
 301 cacctggctc gggtacctct tctaccgaca gcagctgcgc agggctcgga atcgctaccc
 361 taaaggccac tcgaaaaccc agccccgcct cttcaatgga gtgaaggtgc ttcccatccc
 421 tgtcctctcg gacaactaca gctacctcat catcgacacc caggcccagc tggctgtggc
 481 tgtggaccct tcagaccctc gggctgtgca ggcttccatt gaaaaggaag gggtcacctt
 541 ggtcgccatt ctgtgtactc acaagcactg gaccacagt ggagggaacc gtgacctcag
 601 ccggcggcac cgggactgtc gggtgtacgg gagccctcag gacggcatcc cctacctcac
 661 ccatccctg tgtcatcaag atgtggtcag cgtgggacgg cttcagatcc gggccctggc
 721 tacacctggc cacacacaag gccatctggt ctacctactg gatggggagc cctacaaggg
 781 tccctcctgc ctcttctcag gggacctgct cttcctctct ggctgtgggc ggacctttga
 841 gggcaatgca gagaccatgc tgagctcact ggacactgtg ctggggctag gggatgacac
 901 ccttctgtgg cctggtcatg agtatgcaga ggagaacctg gcctttgcag gtgtggtgga
 961 gcccgagaac ctggcccggg agaggaagat gcagtgggtg cagcggcagc ggctggagcg
1021 caagggcacg tgcccatcta ccctgggaga ggagcgctcc tacaaccgt tcctgagaac
1081 ccactgcctg gcgctacagg aggctctggg gccggggccg ggccccactg ggatgatga
1141 ctactcccgg gcccagctcc tggaagagct ccgccggctg aaggatatgc acaagagcaa
1201 gtgatgcccc cagcgcccc agcccagccc actcccgca tgggaggcc gccaccacca
1261 acacctcatc atccttctca tcgctaacac caccacctcc atcggcaccc aagcgggcat
1321 catcccccca cactgctcag gggaggggag ggatcaggcg atgagactgt gaggccaaaa
1381 gaagcgggcc tgttggaggc tgggaacccc gcagcgcgag gctgcctcat caacggcaag
1441 aggaaaggag gggtctcggg acatctccag accctaccaa ctgggagggt cccctcctcc
1501 ttccctactc ctggacgggc agcaaggaca tggggctgc tgttagcttc tccgtcagga
1561 ggcctcactc actgtagccc tggaacccag ggtccatctt gcccttcccc catccatggt
1621 tgggaaagaa gctcagcccc tcacagtggc ctcaagtgtg atgccttaca aaagcaccac
1681 tcagatgggc agctggactc tggtgtcctg agactctgcc ctcttcccac agcctccctg
1741 ccccacccat ccctgcaaag ccatttttca gacagagcca ttcctaagaa cactgaaggg
1801 ctggaatgct ggctggccac tctctgcctc agtggcctcc ctacagcctg gaagaaggag
1861 ggtcctgatt gccaaggaaa cctctcctca ttgggctaag gagacactgg agtctggagt
1921 gtggagcccc acagtcttgc aggtcacatg ctctccttgc acatctggcc tggttgtacc
1981 cactggcctc tgcctctgcc ctgggccaaa agggcccctc cttgccaggg gagagacagc
2041 cacggtcctc tttggccgat gctgtattct cattttggcc cttgttctta ggcccgtctg
2101 cccgccttcc tccatctaac cttttcctgtt ttatccgcag ccctttcttt ctttgagtta
2161 gtaaagattt attctgtaac ctgacactca tctggccctt tgcagtttgc cagccatatt
2221 cccatgtgat ttcccactgg atccaggccc ccatccgctt ggcaggaggg ggctctgacg
2281 tgcaggttgg aaatcagaag tctgtgagag cgcgggagtg catggcagct ctgggtccca
2341 gacctggccc gaccctctg cttcacctcc agctctgctg ctcctctact cttgggttga
2401 gatcccttg gagccacagc gaggaaccct gtggtcctca ggcaggtgta ccttgagtca
2461 gccaggagcc ctcttttcct gtgtcaaagc ctgccctcgg gctctgctca cctctggtga
2521 ccctccaaga tgcccctgcc ctcagtttcc cctcatgatc tggcctctgc ccccttctct
2581 agccacagcc tctagtacac tttagcaata ccaccagact agttagagtt ccgcactcac
2641 caagcaagac atacagtttc atgcctctgt gccttcgctc atgctgtttc ttccgactgg
2701 aatgccttcc cctgctcctc ctgccttgtc tgcctggcaa gttcatctct cacgatcccc
2761 tcaaaggccc cctcctccag gaaggcaacc cctgtgcccc tccctccag gctacctctg
2821 cactttgtca atgcttctct tgtggcactt atcacgctgt attttacttg tttacatgtt
2881 tgtctcccct tctagactgt gaatccttaa gggcatggac tgtatcttat gcatctctgt
2941 atttctgcgc ctagcacggt gcctagcaca cagtaggcgc tcaataaatg ttgaatgaat
3001 gaatgattta atcaagaaaa aaaaaaaaa aa
```

Figure 4.

Mutant human MR-1 nucleic acid sequence (C51T) and (C57T) (SEQ ID NO: 4)

```
   1 actattcccg gcggggagcg cggtgaagcg ggggtgggat ctgaacatgg cggcggtggt
  61 agctgttacg gtgctgaaga gccgggggc gagaaatgcc cgcgtcctcc gggggattct
 121 cgcaggagcc acagctaaca aggtttctca taacaggacc cgggccctgc aaagccacag
 181 ctcctcagag ggcaaggagg aacctgaacc cctatccccg gagctggaat acattcccag
 241 aaagaggggc aagaacccca tgaaagctgt gggactggcc tggtacagcc tgtacacccg
 301 cacctggctc gggtacctct tctaccgaca gcagctgcgc agggctcgga atcgctaccc
 361 taaaggccac tcgaaaaccc agccccgcct cttcaatgga gtgaaggtgc ttcccatccc
 421 tgtcctctcg gacaactaca gctacctcat catcgacacc caggcccagc tggctgtggc
 481 tgtggaccct tcagaccctc gggctgtgca ggcttccatt gaaaaggaag gggtcacctt
 541 ggtcgccatt ctgtgtactc acaagcactg gaccacagt ggagggaacc gtgacctcag
 601 ccggcggcac cgggactgtc gggtgtacgg gagccctcag gacggcatcc cctacctcac
 661 ccatcccctg tgtcatcaag atgtggtcag cgtgggacgg cttcagatcc gggccctggc
 721 tacacctggc cacacacaag gccatctggt ctacctactg gatggggagc cctacaaggg
 781 tccctcctgc ctcttctcag gggacctgct cttcctctct ggctgtgggc ggacctttga
 841 gggcaatgca gagaccatgc tgagctcact ggacactgtg ctggggctag gggatgacac
 901 ccttctgtgg cctggtcatg agtatgcaga ggagaacctg ggctttgcag gtgtggtgga
 961 gcccgagaac ctggcccggg agaggaagat gcagtgggtg cagcggcagc ggctggagcg
1021 caagggcacg tgcccatcta ccctgggaga ggagcgctcc tacaacccgt tcctgagaac
1081 ccactgcctg gcgctacagg aggctctggg gccggggccg ggccccactg gggatgatga
1141 ctactcccgg gcccagctcc tggaagagct ccgccggctg aaggatatgc acaagagcaa
1201 gtgatgcccc cagcgccccc agcccagccc actccccgca tggggaggcc gccaccacca
1261 acacctcatc atccttctca tcgctaacac caccacctcc atcggcaccc aagcgggcat
1321 catccccca cactgctcag gggaggggag ggatcaggcg atgagactgt gaggccaaaa
1381 gaagcgggcc tgttggaggc tgggaaccc gcagcgcgag gctgcctcat caacggcaag
1441 aggaaaggag gggtctcggg acatctccag accctaccaa ctgggagggt cccctcctcc
1501 ttccctactc ctgggacggc agcaaggaca tggggggctgc tgttagcttc tccgtcagga
1561 ggcctcactc actgtagccc tggaacccag ggtccatctt gcccttcccc catccatggt
1621 tgggaaagaa gctcagcccc tcacagtggc ctcaagtgtg atgccttaca aaagcaccac
1681 tcagatgggc agctggactc tggtgtcctg agactctgcc ctcttcccac agcctccctg
1741 ccccacccat ccctgcaaag ccattttca gacagagcca ttcctaagaa cactgaaggg
1801 ctggaatgct ggctggccac tctctgcctc agtggcctcc ctacagcctg gaagaaggag
1861 ggtcctgatt gccaaggaaa cctctcctca ttgggctaag gagacactgg agtctggagt
1921 gtggagcccc acagtcttgc aggtcacatg ctctccttgc acatctggtc tggttgtacc
1981 cactggcctc tgcctctgcc ctgggccaaa agggccctc cttgccaggg gagagacagc
2041 cacggtcctc tttggccgat gctgtattct catttggcc cttgttctta ggcccgtctg
2101 cccgccttcc tccatctaac ctttcctgtt ttatccgcag ccctttttctt ctttgagtta
2161 gtaaagattt attctgtaac ctgacactca tctggccctt tgcagtttgc cagccatatt
2221 cccatgtgat ttcccactgg atccaggccc catcctgct ggcaggaggg ggctctgacg
2281 tgcaggttgg aaatcagaag tctgtgagag cgcgggagtg catggcagct ctgggtccca
2341 gacctggccc gaccctctg cttcacctcc agctctgctg ctcctctact cttgggttga
2401 gatcctttg gagccacagc gaggaaccct gtggtcctca ggcaggtgta ccttgagtca
2461 gccaggagcc ctcttttcct gtgtcaaagc ctgccctcgg gctctgctca cctctggtga
2521 ccctccaaga tgcccctgcc ctcagtttcc cctcatgatc tggcctctgc cccttctct
2581 agccacagcc tctagtacac tttagcaata ccaccagact agttagagtt ccgcactcac
2641 caagcaagac atacagtttc atgcctctgt gccttcgctc atgctgtttc ttccgactgg
2701 aatgccttcc cctgctcctc ctgccttgtc tgcctggcaa gttcatctct cacgatcccc
2761 tcaaaggccc cctcctccag gaaggcaacc cctgtgcccc tcccctccag gctacctctg
2821 cactttgtca atgcttctct tgtggcactt atcacgctgt attttacttg tttacatgtt
2881 tgtctcccct tctagactgt gaatccttaa gggcatggac tgtatcttat gcatctctgt
2941 atttctgcgc ctagcacggt gcctagcaca cagtaggcgc tcaataaatg ttgaatgaat
3001 gaatgattta atcaagaaaa aaaaaaaaa aa
```

Figure 5.
Wild Type human MR-1 amino acid sequence (SEQ ID NO: 5)

MAAVVAATALKGRGARNARVLRGILAGATANKASHNRTRALQSHSSPEGKEEP
EPLSPELEYIPRKRGKNPMKAVGLAWAIGFPCGILLFILTKREVDKDRVKQMKAR
QNMRLSNTGEYESQRFRASSQSAPSPDVGSGVQT

Figure 6.
Mutant human MR-1 amino acid sequence (SEQ ID NO: 6)

MAAVVAVTALKGRGARNARVLRGILAGATANKASHNRTRALQSHSSPEGKEEP
EPLSPELEYIPRKRGKNPMKAVGLAWAIGFPCGILLFILTKREVDKDRVKQMKAR
QNMRLSNTGEYESQRFRASSQSAPSPDVGSGVQT

Figure 7.
Mutant human MR-1 amino acid sequence (SEQ ID NO: 7)

MAAVVAATVLKGRGARNARVLRGILAGATANKASHNRTRALQSHSSPEGKEEP
EPLSPELEYIPRKRGKNPMKAVGLAWAIGFPCGILLFILTKREVDKDRVKQMKAR
QNMRLSNTGEYESQRFRASSQSAPSPDVGSGVQT

Figure 8.
Mutant human MR-1 amino acid sequence (SEQ ID NO: 8)

MAAVVAVTVLKGRGARNARVLRGILAGATANKASHNRTRALQSHSSPEGKEE
PEPLSPELEYIPRKRGKNPMKAVGLAWAIGFPCGILLFILTKREVDKDRVKQMKA
RQNMRLSNTGEYESQRFRASSQSAPSPDVGSGVQT

SEQUENCE LISTING

```
<160> NUMBER OF SEQ ID NOS: 14

<210> SEQ ID NO 1
<211> LENGTH: 3032
<212> TYPE: DNA
<213> ORGANISM: Homo sapiens

<400> SEQUENCE: 1
actattcccg gcggggagcg cggtgaagcg ggggtgggat ctgaacatgg cggcggtggt      60
agctgctacg gcgctgaaga gccgggggggc gagaaatgcc cgcgtcctcc gggggattct     120
cgcaggagcc acagctaaca aggtttctca taacaggacc cgggccctgc aaagccacag     180
ctcctcagag ggcaaggagg aacctgaacc cctatccccg gagctggaat acattcccag     240
aaagaggggc aagaacccca tgaaagctgt gggactggcc tggtacagcc tgtacacccg     300
cacctggctc gggtacctct tctaccgaca gcagctgcgc agggctcgga atcgctaccc     360
taaaggccac tcgaaaaccc agccccgcct cttcaatgga gtgaaggtgc ttcccatccc     420
tgtcctctcg gacaactaca gctacctcat catcgcacac caggcccagc tggctgtggc     480
tgtggaccct tcagaccctc gggctgtgca ggcttccatt gaaaaggaag gggtcacctt     540
ggtcgccatt ctgtgtactc acaagcactg ggaccacagt ggagggaacc gtgacctcag     600
ccggcggcac cgggactgtc gggtgtacgg gagccctcag gacggcatcc cctacctcac     660
ccatcccctg tgtcatcaag atgtggtcag cgtgggacgg cttcagatcc gggccctggc     720
```

```
tacacctggc cacacacaag gccatctggt ctacctactg gatggggagc cctacaaggg      780
tccctcctgc ctcttctcag gggacctgct cttcctctct ggctgtgggc ggacctttga      840
gggcaatgca gagaccatgc tgagctcact ggacactgtg ctggggctag ggatgacac       900
ccttctgtgg cctggtcatg agtatgcaga ggagaacctg ggctttgcag gtgtggtgga      960
gcccgagaac ctggcccggg agaggaagat gcagtgggtg cagcggcagc ggctggagcg     1020
caagggcacg tgcccatcta ccctgggaga ggagcgctcc tacaacccgt tcctgagaac     1080
ccactgcctg cgctacagg aggctctggg gccggggccg ggccccactg ggatgatga       1140
ctactcccgg gcccagctcc tggaagagct ccgccggctg aaggatatgc acaagagcaa     1200
gtgatgcccc cagcgccccc agcccagccc actccccgca tggggaggcc gccaccacca     1260
acacctcatc atccttctca tcgctaacac caccacctcc atcggcaccc aagcgggcat     1320
catccccca cactgctcag gggaggggag ggatcaggcg atgagactgt gaggccaaaa      1380
gaagcgggcc tgttggaggc tgggaacccc gcagcgcgag gctgcctcat caacggcaag     1440
aggaaaggag gggtctcggg acatctccag accctaccaa ctgggagggt cccctcctcc     1500
ttccctactc ctgggacggc agcaaggaca tgggggctgc tgttagcttc tccgtcagga     1560
ggcctcactc actgtagccc tggaacccag ggtccatctt gcccttcccc catccatggt     1620
tgggaaagaa gctcagcccc tcacagtggc ctcaagtgtg atgccttaca aaagcaccac     1680
tcagatgggc agctggactc tggtgtcctg agactctgcc ctcttcccac agcctccctg     1740
ccccacccat ccctgcaaag ccattttcca gacagagcca ttcctaagaa cactgaaggg     1800
ctggaatgct ggctggccac tctctgcctc agtggcctcc ctacagcctg gaagaaggag     1860
ggtcctgatt gccaaggaaa cctctcctca ttgggctaag gagacactgg agtctggagt     1920
gtggagcccc acagtcttgc aggtcacatg ctctccttgc acatctggcc tggttgtacc     1980
cactggcctc tgcctctgcc ctgggccaaa agggcccctc cttgccaggg gagagacagc     2040
cacggtcctc tttggccgat gctgtattct cattttggcc cttgttctta ggcccgtctg     2100
cccgccttcc tccatctaac cttcctgtt ttatccgcag cccttttctt ctttgagtta      2160
gtaaagattt attctgtaac ctgacactca tctggccctt gcagtttgc cagccatatt      2220
cccatgtgat ttcccactgg atccaggccc ccatccggct ggcaggaggg ggctctgacg     2280
tgcaggttgg aaatcagaag tctgtgagag cgcgggagtg catggcagct ctgggtccca     2340
gacctggccc gaccccctctg cttcacctcc agctctgctg ctcctctact cttgggttga    2400
gatccctttg gagccacagc gaggaaccct gtggtcctca ggcaggtgta ccttgagtca     2460
gccaggagcc ctcttttcct gtgtcaaagc ctgccctcgg gctctgctca cctctggtga    2520
ccctccaaga tgcccctgcc ctcagtttcc cctcatgatc tggcctctgc ccccttctct    2580
agccacagcc tctagtacac tttagcaata ccaccagact agttagagtt ccgcactcac    2640
caagcaagac atacagtttc atgcctctgt gccttcgctc atgctgtttc ttccgactgg    2700
aatgccttcc cctgctcctc ctgccttgtc tgcctggcaa gttcatctct cacgatcccc    2760
tcaaaggccc cctcctccag gaaggcaacc cctgtgcccc tccctccag gctacctctg     2820
cactttgtca atgcttctct tgtggcactt atcacgctgt attttacttg tttacatgtt    2880
tgtctcccct tctagactgt gaatccttaa gggcatggac tgtatcttat gcatctctgt    2940
atttctgcgc ctagcacggt gcctagcaca cagtaggcgc tcaataaatg ttgaatgaat    3000
gaatgattta atcaagaaaa aaaaaaaaaa aa                                    3032
```

```
<210> SEQ ID NO 2
<211> LENGTH: 3032
<212> TYPE: DNA
<213> ORGANISM: Homo sapiens

<400> SEQUENCE: 2
actattcccg gcggggagcg cggtgaagcg ggggtgggat ctgaacatgg cggcggtggt      60
agctgttacg gcgctgaaga gccgggggggc gagaaatgcc cgcgtcctcc ggggattct    120 cgcaggagcc acagctaaca aggtttctca taacaggacc cgggccctgc aaagccacag   180
ctcctcagag ggcaaggagg aacctgaacc cctatccccg gagctggaat acattcccag   240 aaagagggggc aagaacccca tgaaagctgt gggactggcc tggtacagcc tgtacacccg   300
cacctggctc gggtacctct tctaccgaca gcagctgcgc agggctcgga atcgctaccc   360
taaaggccac tcgaaaaccc agccccgcct cttcaatgga gtgaaggtgc ttcccatccc   420
tgtcctctcg gacaactaca gctacctcat catcgacacc caggcccagc tggctgtggc   480 tgtggacccct tcagaccctc gggctgtgca ggcttccatt gaaaaggaag gggtcacctt   540
ggtcgccatt ctgtgtactc acaagcactg gaccacagt ggagggaacc gtgacctcag    600
ccggcggcac cgggactgtc gggtgtacgg gagccctcag gacggcatcc cctacctcac   660 ccatccccctg tgtcatcaag atgtggtcag cgtgggacgg cttcagatcc gggccctggc   720
tacacctggc cacacacaag gccatctggt ctacctactg gatggggagc cctacaaggg   780
tccctcctgc ctcttctcag gggacctgct cttcctctct ggctgtgggc ggaccttga   840 gggcaatgca gagaccatgc tgagctcact ggacactgtg ctggggctag ggatgacac    900 ccttctgtgg cctggtcatg agtatgcaga ggagaacctg ggctttgcag gtgtggtgga   960
gcccgagaac ctggccccggg agaggaagat gcagtgggtg cagcggcagc ggctggagcg   1020
caagggcacg tgcccatcta ccctgggaga ggagcgctcc tacaacccgt tcctgagaac   1080
ccactgcctg gcgctacagg aggctctggg gccggggccg ggcccactg gggatgatga   1140 ctactcccgg gcccagctcc tggaagagct ccgccggctg aaggatatgc acaagagcaa   1200
gtgatgcccc cagcgccccc agcccagccc actccccgca tggggaggcc gccaccacca   1260
acacctcatc atccttctca tcgctaacac caccacctcc atcggcaccc aagcgggcat   1320
catcccccca cactgctcag gggaggggag ggatcaggcg atgagactgt gaggccaaaa   1380
gaagcgggcc tgttggaggc tgggaacccc gcagcgcgag gctgcctcat caacggcaag   1440
aggaaaggag gggtctcggg acatctccag accctaccaa ctgggagggt ccctcctcc    1500 ttccctactc ctgggacggc agcaaggaca tgggggctgc tgttagcttc tccgtcagga   1560
ggcctcactc actgtagccc tggaaccag gtccatctt gcccttcccc catccatggt    1620
tgggaaagaa gctcagcccc tcacagtggc ctcaagtgtg atgccttaca aaagcaccac   1680
tcagatgggc agctggactc tggtgtcctg agactctgcc ctcttcccac agcctccctg   1740
ccccacccat ccctgcaaag ccattttttca gacagagcca ttcctaagaa cactgaaggg   1800
ctggaatgct ggctggccac tctctgcctc agtggcctcc ctacagcctg aagaaggag    1860 ggtcctgatt gccaaggaaa cctctcctca ttgggctaag gagacactgg agtctggagt   1920
gtggagcccc acagtcttgc aggtcacatg ctctccttgc acatctggcc tggttgtacc   1980
cactggcctc tgcctctgcc ctgggccaaa agggcccctc cttgccaggg gagagacagc   2040
cacggtcctc tttggccgat gctgtattct cattttggcc cttgttctta ggcccgtctg   2100
cccgccttcc tccatctaac cttccctgtt ttatccgcag ccctttttctt ctttgagtta   2160 gtaaagattt attctgtaac ctgacactca tctggcccctt tgcagtttgc cagccatatt   2220
```

```
cccatgtgat ttcccactgg atccaggccc catccggct ggcaggaggg ggctctgacg    2280
tgcaggttgg aaatcagaag tctgtgagag cgcgggagtg catggcagct ctgggtccca    2340
gacctggccc gacccctctg cttcacctcc agctctgctg ctcctctact cttgggttga    2400 gatcccttg gagccacagc gaggaaccct gtggtcctca ggcaggtgta ccttgagtca    2460
gccaggagcc ctcttttcct gtgtcaaagc ctgccctcgg gctctgctca cctctggtga    2520
ccctccaaga tgcccctgcc ctcagtttcc cctcatgatc tggcctctgc cccttctct    2580 agccacagcc tctagtacac tttagcaata ccaccagact agttagagtt ccgcactcac    2640
caagcaagac atacagtttc atgcctctgt gccttcgctc atgctgtttc ttccgactgg    2700
aatgccttcc cctgctcctc ctgccttgtc tgcctggcaa gttcatctct cacgatcccc    2760
tcaaaggccc cctcctccag gaaggcaacc cctgtgcccc tcccctccag gctacctctg    2820
cactttgtca atgcttctct tgtggcactt atcacgctgt attttacttg tttacatgtt    2880
tgtctcccct tctagactgt gaatccttaa gggcatggac tgtatcttat gcatctctgt    2940
atttctgcgc ctagcacggt gcctagcaca cagtaggcgc tcaataaatg ttgaatgaat    3000
gaatgattta atcaagaaaa aaaaaaaaaa aa                                 3032

<210> SEQ ID NO 3
<211> LENGTH: 3032
<212> TYPE: DNA
<213> ORGANISM: Homo sapiens

<400> SEQUENCE: 3
actattcccg gcggggagcg cggtgaagcg ggggtgggat ctgaacatgg cggcggtggt      60
agctgctacg gtgctgaaga gccgggggc gagaaatgcc cgcgtcctcc gggggattct     120
cgcaggagcc acagctaaca aggtttctca taacaggacc cgggccctgc aaagccacag     180
ctcctcagag ggcaaggagg aacctgaacc cctatccccg gagctggaat acattcccag     240
aaagaggggc aagaacccca tgaaagctgt gggactggcc tggtacagcc tgtacacccg     300
cacctggctc gggtacctct tctaccgaca gcagctgcgc agggctcgga atcgctaccc     360
taaaggccac tcgaaaaccc agccccgcct cttcaatgga gtgaaggtgc ttcccatccc     420
tgtcctctcg gacaactaca gctacctcat catcgacacc caggcccagc tggctgtggc     480
tgtggaccct tcagaccctc gggctgtgca ggcttccatt gaaaaggaag gggtcacctt     540
ggtcgccatt ctgtgtactc acaagcactg ggaccacagt ggagggaacc gtgacctcag     600
ccggcggcac cgggactgtc gggtgtacgg gagccctcag gacggcatcc cctacctcac     660
ccatcccctg tgtcatcaag atgtggtcag cgtgggacgg cttcagatcc gggccctggc     720
tacacctggc cacacacaag gccatctggt ctacctactg gatggggagc cctacaaggg     780 tcctcctgc ctcttctcag gggacctgct cttcctctct ggctgtgggc gaccttttga     840
gggcaatgca gagaccatgc tgagctcact ggacactgtg ctggggctag ggatgacac      900 ccttctgtgg cctggtcatg agtatgcaga ggagaacctg ggcttgcag gtgtggtgga     960 gcccgagaac ctggcccggg agaggaagat gcagtgggtg cagcggcagc ggctggagcg    1020
caagggcacg tgcccatcta ccctgggaga ggagcgctcc tacaacccgt tcctgagaac    1080
ccactgcctg gcgctacagg aggctctggg gccggggccg ggcccactg gggatgatga    1140 ctactcccgg gcccagctcc tggaagagct ccgccggctg aaggatatgc acaagagcaa    1200
gtgatgcccc cagcgccccc agcccagccc actcccgca tggggaggcc gccaccacca    1260
acacctcatc atccttctca tcgctaacac caccacctcc atcggcaccc aagcgggcat    1320
```

-continued

| | |
|---|---|
| catcccccca cactgctcag gggaggggag ggatcaggcg atgagactgt gaggccaaaa | 1380 |
| gaagcgggcc tgttggaggc tgggaacccc gcagcgcgag gctgcctcat caacggcaag | 1440 |
| aggaaaggag gggtctcggg acatctccag accctaccaa ctgggagggt cccctcctcc | 1500 |
| ttccctactc ctgggacggc agcaaggaca tgggggctgc tgttagcttc tccgtcagga | 1560 |
| ggcctcactc actgtagccc tggaaccag ggtccatctt gcccttcccc catccatggt | 1620 |
| tgggaaagaa gctcagcccc tcacagtggc ctcaagtgtg atgccttaca aaagcaccac | 1680 |
| tcagatgggc agctggactc tggtgtcctg agactctgcc ctcttcccac agcctccctg | 1740 |
| ccccacccat ccctgcaaag ccattttttca gacagagcca ttcctaagaa cactgaaggg | 1800 |
| ctggaatgct ggctggccac tctctgcctc agtggcctcc ctacagcctg aagaaggag | 1860 |
| ggtcctgatt gccaaggaaa cctctcctca ttgggctaag gagacactgg agtctggagt | 1920 |
| gtggagcccc acagtcttgc aggtcacatg ctctccttgc acatctggcc tggttgtacc | 1980 |
| cactggcctc tgcctctgcc ctgggccaaa agggccccctc cttgccaggg gagagacagc | 2040 |
| cacggtcctc tttggccgat gctgtattct cattttggcc cttgttctta ggcccgtctg | 2100 |
| cccgccttcc tccatctaac cttttcctgtt ttatccgcag ccctttttctt ctttgagtta | 2160 |
| gtaaagattt attctgtaac ctgacactca tctggcccctt tgcagtttgc cagccatatt | 2220 |
| cccatgtgat ttcccactgg atccaggccc ccatccggct ggcaggaggg ggctctgacg | 2280 |
| tgcaggttgg aaatcagaag tctgtgagag cgcgggagtg catggcagct ctgggtccca | 2340 |
| gacctggccc gacccctctg cttcacctcc agctctgctg ctcctctact cttgggttga | 2400 |
| gatcccttttg gagccacagc gaggaaccct gtggtcctca ggcaggtgta ccttgagtca | 2460 |
| gccaggagcc ctcttttcct gtgtcaaagc ctgcccctcgg gctctgctca cctctggtga | 2520 |
| ccctccaaga tgcccctgcc ctcagtttcc cctcatgatc tggcctctgc cccttctct | 2580 |
| agccacagcc tctagtacac tttagcaata ccaccagact agttagagtt ccgcactcac | 2640 |
| caagcaagac atacagttttc atgcctctgt gccttcgctc atgctgtttc ttccgactgg | 2700 |
| aatgccttcc cctgctcctc ctgccttgtc tgcctggcaa gttcatctct cacgatcccc | 2760 |
| tcaaaggccc cctcctccag gaaggcaacc cctgtgcccc tcccctccag gctacctctg | 2820 |
| cactttgtca atgcttctct tgtggcactt atcacgctgt attttacttg tttacatgtt | 2880 |
| tgtctcccct tctagactgt gaatccttaa gggcatggac tgtatcttat gcatctctgt | 2940 |
| atttctgcgc ctagcacggt gcctagcaca cagtaggcgc tcaataaatg ttgaatgaat | 3000 |
| gaatgattta atcaagaaaa aaaaaaaaaa aa | 3032 |

<210> SEQ ID NO 4
<211> LENGTH: 3032
<212> TYPE: DNA
<213> ORGANISM: Homo sapiens

<400> SEQUENCE: 4

| | |
|---|---|
| actattcccg gcggggagcg cggtgaagcg ggggtgggat ctgaacatgg cggcggtggt | 60 |
| agctgttacg gtgctgaaga gccgggggggc gagaaatgcc cgcgtcctcc ggggattct | 120 |
| cgcaggagcc acagctaaca aggtttctca taacaggacc cgggccctgc aaagccacag | 180 |
| ctcctcagag ggcaaggagg aacctgaacc cctatcccccg gagctggaat acattccag | 240 |
| aaagaggggc aagaaccca tgaaagctgt gggactggcc tggtacagcc tgtacacccg | 300 |
| cacctggctc gggtacctct tctaccgaca gcagctgcgc agggctcgga atcgctaccc | 360 |
| taaaggccac tcgaaaaccc agccccgcct cttcaatgga gtgaaggtgc ttcccatccc | 420 |

```
tgtcctctcg gacaactaca gctacctcat catcgacacc caggcccagc tggctgtggc    480
tgtggaccct tcagccctc gggctgtgca ggcttccatt gaaaaggaag gggtcacctt     540
ggtcgccatt ctgtgtactc acaagcactg ggaccacagt ggagggaacc gtgacctcag    600
ccggcggcac cgggactgtc gggtgtacgg gagccctcag gacggcatcc cctacctcac    660 ccatccctg tgtcatcaag atgtggtcag cgtgggacgg cttcagatcc gggccctggc    720
tacacctggc cacacacaag gccatctggt ctacctactg gatggggagc cctacaaggg    780
tccctcctgc ctcttctcag ggacctgct cttcctctct ggctgtgggc ggaccttga     840 gggcaatgca gagaccatgc tgagctcact ggacactgtg ctggggctag ggatgacac    900 ccttctgtgg cctggtcatg agtatgcaga ggagaacctg ggcttgcag gtgtggtgga    960 gcccgagaac ctggcccggg agaggaagat gcagtgggtg cagcggcagc ggctggagcg   1020
caagggcacg tgcccatcta ccctgggaga ggagcgctcc tacaacccgt tcctgagaac   1080
ccactgcctg gcgctacagg aggctctggg gccggggccg ggcccactg gggatgatga    1140 ctactcccgg gcccagctcc tggaagagct ccgccggctg aaggatatgc acaagagcaa   1200
gtgatgcccc cagcgccccc agcccagccc actccccgca tggggaggcc gccaccacca   1260
acacctcatc atccttctca tcgctaacac caccacctcc atcggcaccc aagcgggcat   1320
catcccccca cactgctcag gggaggggag ggatcaggcg atgagactgt gaggccaaaa   1380
gaagcgggcc tgttggaggc tgggaacccc gcagcgcgag gctgcctcat caacggcaag   1440
aggaaaggag gggtctcggg acatctccag accctaccaa ctgggagggt ccctcctcc    1500 ttccctactc ctgggacggc agcaaggaca tgggggctgc tgttagcttc tccgtcagga   1560
ggcctcactc actgtagccc tggaaccag ggtccatctt gcccttcccc catccatggt    1620
tgggaaagaa gctcagcccc tcacagtggc ctcaagtgtg atgccttaca aaagcaccac   1680
tcagatgggc agctggactc tggtgtcctg agactctgcc ctcttcccac agcctccctg   1740
ccccacccat ccctgcaaag ccattttca gacagagcca ttcctaagaa cactgaaggg    1800
ctggaatgct ggctggccac tctctgcctc agtggcctcc ctacagcctg aagaaggag    1860 ggtcctgatt gccaaggaaa cctctcctca ttgggctaag gagacactgg agtctggagt   1920
gtggagcccc acagtcttgc aggtcacatg ctctccttgc acatctggcc tggttgtacc   1980
cactggcctc tgcctctgcc ctgggccaaa agggcccctc cttgccaggg gagagacagc   2040
cacggtcctc tttggccgat gctgtattct catttggcc cttgttctta ggccgtctg     2100 cccgccttcc tccatctaac cttcctgtt ttatccgcag ccctttctt ctttgagtta     2160 gtaaagattt attctgtaac ctgacactca tctggccctt tgcagtttgc cagccatatt   2220
cccatgtgat ttcccactgg atccaggccc ccatccggct ggcaggaggg ggctctgacg   2280
tgcaggttgg aaatcagaag tctgtgagag cgcgggagtg catggcagct ctgggtccca   2340
gacctggccc gaccctctg cttcacctcc agctctgctg ctcctctact cttgggttga    2400 gatcccttg gagccacagc gaggaaccct gtggtcctca ggcaggtgta ccttgagtca    2460
gccaggagcc ctcttttcct gtgtcaaagc ctgccctcgg gctctgctca cctctggtga   2520
ccctccaaga tgcccctgcc ctcagttcc cctcatgatc tggcctctgc cccttctct    2580 agccacagcc tctagtacac tttagcaata ccaccagact agttagagtt ccgcactcac   2640
caagcaagac atacagtttc atgcctctgt gccttcgctc atgctgtttc ttccgactgg   2700
aatgccttcc cctgctcctc ctgccttgtc tgcctggcaa gttcatctct cacgatcccc   2760
tcaaaggccc cctcctccag gaaggcaacc cctgtgcccc tcccctccag gctacctctg   2820
```

```
cactttgtca atgcttctct tgtggcactt atcacgctgt attttacttg tttacatgtt    2880
tgtctcccct tctagactgt gaatccttaa gggcatggac tgtatcttat gcatctctgt    2940
atttctgcgc ctagcacggt gcctagcaca cagtaggcgc tcaataaatg ttgaatgaat    3000
gaatgattta atcaagaaaa aaaaaaaaaa aa                                  3032
```

<210> SEQ ID NO 5
<211> LENGTH: 142
<212> TYPE: PRT
<213> ORGANISM: Homo sapiens

<400> SEQUENCE: 5

```
Met Ala Ala Val Val Ala Ala Thr Ala Leu Lys Gly Arg Gly Ala Arg
1               5                   10                  15

Asn Ala Arg Val Leu Arg Gly Ile Leu Ala Gly Ala Thr Ala Asn Lys
            20                  25                  30

Ala Ser His Asn Arg Thr Arg Ala Leu Gln Ser His Ser Ser Pro Glu
        35                  40                  45

Gly Lys Glu Glu Pro Glu Pro Leu Ser Pro Glu Leu Glu Tyr Ile Pro
    50                  55                  60

Arg Lys Arg Gly Lys Asn Pro Met Lys Ala Val Gly Leu Ala Trp Ala
65                  70                  75                  80

Ile Gly Phe Pro Cys Gly Ile Leu Leu Phe Ile Leu Thr Lys Arg Glu
                85                  90                  95

Val Asp Lys Asp Arg Val Lys Gln Met Lys Ala Arg Gln Asn Met Arg
            100                 105                 110

Leu Ser Asn Thr Gly Glu Tyr Glu Ser Gln Arg Phe Arg Ala Ser Ser
        115                 120                 125

Gln Ser Ala Pro Ser Pro Asp Val Gly Ser Gly Val Gln Thr
    130                 135                 140
```

<210> SEQ ID NO 6
<211> LENGTH: 142
<212> TYPE: PRT
<213> ORGANISM: Homo sapiens

<400> SEQUENCE: 6

```
Met Ala Ala Val Val Ala Val Thr Ala Leu Lys Gly Arg Gly Ala Arg
1               5                   10                  15

Asn Ala Arg Val Leu Arg Gly Ile Leu Ala Gly Ala Thr Ala Asn Lys
            20                  25                  30

Ala Ser His Asn Arg Thr Arg Ala Leu Gln Ser His Ser Ser Pro Glu
        35                  40                  45

Gly Lys Glu Glu Pro Glu Pro Leu Ser Pro Glu Leu Glu Tyr Ile Pro
    50                  55                  60

Arg Lys Arg Gly Lys Asn Pro Met Lys Ala Val Gly Leu Ala Trp Ala
65                  70                  75                  80

Ile Gly Phe Pro Cys Gly Ile Leu Leu Phe Ile Leu Thr Lys Arg Glu
                85                  90                  95

Val Asp Lys Asp Arg Val Lys Gln Met Lys Ala Arg Gln Asn Met Arg
            100                 105                 110

Leu Ser Asn Thr Gly Glu Tyr Glu Ser Gln Arg Phe Arg Ala Ser Ser
        115                 120                 125

Gln Ser Ala Pro Ser Pro Asp Val Gly Ser Gly Val Gln Thr
    130                 135                 140
```

```
<210> SEQ ID NO 7
<211> LENGTH: 142
<212> TYPE: PRT
<213> ORGANISM: Homo sapiens

<400> SEQUENCE: 7

Met Ala Val Val Ala Val Thr Val Leu Lys Gly Arg Gly Ala Arg
1               5                   10                  15

Asn Ala Arg Val Leu Arg Gly Ile Leu Ala Gly Ala Thr Ala Asn Lys
            20                  25                  30

Ala Ser His Asn Arg Thr Arg Ala Leu Gln Ser His Ser Ser Pro Glu
        35                  40                  45

Gly Lys Glu Glu Pro Glu Pro Leu Ser Pro Glu Leu Glu Tyr Ile Pro
    50                  55                  60

Arg Lys Arg Gly Lys Asn Pro Met Lys Ala Val Gly Leu Ala Trp Ala
65                  70                  75                  80

Ile Gly Phe Pro Cys Gly Ile Leu Leu Phe Ile Leu Thr Lys Arg Glu
                85                  90                  95

Val Asp Lys Asp Arg Val Lys Gln Met Lys Ala Arg Gln Asn Met Arg
                100                 105                 110

Leu Ser Asn Thr Gly Glu Tyr Glu Ser Gln Arg Phe Arg Ala Ser Ser
            115                 120                 125

Gln Ser Ala Pro Ser Pro Asp Val Gly Ser Gly Val Gln Thr
        130                 135                 140

<210> SEQ ID NO 8
<211> LENGTH: 142
<212> TYPE: PRT
<213> ORGANISM: Homo sapiens

<400> SEQUENCE: 8

Met Ala Val Val Ala Val Thr Val Leu Lys Gly Arg Gly Ala Arg
1               5                   10                  15

Asn Ala Arg Val Leu Arg Gly Ile Leu Ala Gly Ala Thr Ala Asn Lys
            20                  25                  30

Ala Ser His Asn Arg Thr Arg Ala Leu Gln Ser His Ser Ser Pro Glu
        35                  40                  45

Gly Lys Glu Glu Pro Glu Pro Leu Ser Pro Glu Leu Glu Tyr Ile Pro
    50                  55                  60

Arg Lys Arg Gly Lys Asn Pro Met Lys Ala Val Gly Leu Ala Trp Ala
65                  70                  75                  80

Ile Gly Phe Pro Cys Gly Ile Leu Leu Phe Ile Leu Thr Lys Arg Glu
                85                  90                  95

Val Asp Lys Asp Arg Val Lys Gln Met Lys Ala Arg Gln Asn Met Arg
                100                 105                 110

Leu Ser Asn Thr Gly Glu Tyr Glu Ser Gln Arg Phe Arg Ala Ser Ser
            115                 120                 125

Gln Ser Ala Pro Ser Pro Asp Val Gly Ser Gly Val Gln Thr
        130                 135                 140

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
atctgaacat ggcggcggtg gtag                                    24
```

```
<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
agtggccttt agggtagcga ttcc                                              24

<210> SEQ ID NO 11
<211> LENGTH: 19
<212> TYPE: DNA
<213> ORGANISM: Homo sapiens

<400> SEQUENCE: 11
ctgctacggy gctgaaggg                                                    19

<210> SEQ ID NO 12
<211> LENGTH: 19
<212> TYPE: DNA
<213> ORGANISM: Homo sapiens

<400> SEQUENCE: 12
ctgctacggc gctgaaggg                                                    19

<210> SEQ ID NO 13
<211> LENGTH: 21
<212> TYPE: DNA
<213> ORGANISM: Homo sapiens

<400> SEQUENCE: 13
gtggtagctg ytacggcgct g                                                 21

<210> SEQ ID NO 14
<211> LENGTH: 21
<212> TYPE: DNA
<213> ORGANISM: Homo sapiens

<400> SEQUENCE: 14
gtggtagctg ctacggcgct g                                                 21
```

METHODS FOR DIAGNOSING EPISODIC MOVEMENT DISORDERS AND RELATED CONDITIONS

CROSS REFERENCE TO RELATED APPLICATIONS

The present application is a continuation of U.S. patent application Ser. No. 11/167,838, filed Jun. 27, 2005, now issued as U.S. patent Ser. No. 7,727,719, which claims priority to U.S. Provisional Patent Application No. 60/583,058, filed Jun. 25, 2004, both of which are herein incorporated by reference in their entireties.

STATEMENT REGARDING FEDERALLY SPONSORED RESEARCH OR DEVELOPMENT

This invention was made with government support under Grant No. 1R01 NS045163-0 awarded by the National Institutes of Health. The government has certain rights in the invention.

FIELD OF THE INVENTION

The present invention provides compositions and methods for research, diagnostic, drug screening, and therapeutic applications related to paroxysmal dystonic choreoathetosis and related conditions. In particular, the present invention provides mutations in the myofibrillogenesis regulator 1 (MR-1) gene associated with such conditions.

BACKGROUND OF THE INVENTION

Episodic phenomena are common in humans. These include (but are not limited to) seizures, headaches, cardiac arrhythmias, episodic movement disorders, and periodic paralyses. These disorders have strong genetic determinants and often affect people who are completely normal between attacks. Although episodic disorders of the brain, heart, and muscle seem quite different on the surface, they share many similarities. They often surface in childhood or adolescence and frequently improve with aging. In addition to being episodic, attacks in all of these disorders can often be precipitated by stress, fatigue, alcohol, and some dietary factors. The medications used to treat these disorders overlap significantly. Thus, insights gained by study of any of these disorders can impact an understanding of other related disorders.

Paroxysmal Dystonic Choreoathetosis (Mendelian Inheritance in Man No. 11880; hereinafter, "PDC"), also known as paroxysmal nonkinesigenic dyskinesia, is an episodic movement disorder in which attacks of dystonia, chorea, and athetosis begin in childhood through early adulthood; involve the extremities, trunk, and face; and may cause dysarthria or dysphagia. These episodes last from several minutes to more than an hour and may occur several times each day (see, e.g., Mount, L. A. and Reback S., Arch Neurol Psychiatry. 1940, 44:841-847; Demirkiran M. and Jankovic J., Ann Neurol. 1995, 38:571-579; Richards R. N. and Barnett, H. J. M. Neurology 1968, 18:461-469; Fahn S. J Neurol Neurosurg Psychiatry 1987, 50:117-118; Lance J. W. Ann Neurol. 1977, 2:285-293; and Nakano T., et al., Clin Neurol. 1982, 23:199-202; each herein incorporated by reference in their entireties). The PDC attacks occur both spontaneously while at rest and following provoking factors that include alcohol or caffeine consumption and to a lesser extent fatigue, hunger, and emotional stress.

A locus for autosomal dominant PDC on chromosome 2q33-2q35 has been identified. A consensus PDC locus interval spanning approximately 2.7 cM between DNA polymorphisms D2S295 and D2S163 has been identified (see, e.g., Fink J. K., et al., Am J Hum Genet. 1996, 59:140-145; Fouad G. T., et al., Am J Hum Genet. 1996, 59:135-139; Jarman P. R., et al., Brain. 1997, 120:2125-2130; Matsuo H., et al., Arch Neurol. 1999, 56:721-726; Hofele K., et al., Neurology. 1997, 49:1252-1257; Przuntek H., et al., J. Neurol. 1983, 230:163-169; and Raskind W. H., et al., Hum Genet. 1998, 102:93-97; Einum D. D., et al., Neurogenetics 1998, 1:289-292; Grunder S., et al., Eur J Hum Genet. 2001, 9:672-676; and Tokarz D., et al., Am J Hum Genet. 2001, 69:629; each herein incorporated by reference in their entireties). This region includes a cluster of ion channel genes (see, e.g., Fink J. K., et al., Am J Hum Genet. 1996, 59:140-145; herein incorporated by reference in its entirety).

Presently, there is no cure for PDC. Medications used to treat PDC include anticonvulsant agents such as phenyloin, primidone, valporate, carbamazepine, phenobarbital, and diazepam, and anticholinergics, levodopa, flunarizine, and tetrabenazine. However, such medications are only used to mask the symptoms of PDC.

What is needed is a better understanding of the pathophysiology, genetics and biochemistry underlying episodic movement disorders such as PDC. Additionally, better treatment options for PDC are needed, and improved forms of diagnosis.

SUMMARY OF THE INVENTION

The present invention provides compositions and methods for research, diagnostic, drug screening, and therapeutic applications related to PDC and related conditions. In particular, the present invention provides mutations in the MR-1 gene associated with such conditions.

Accordingly, in some embodiments, the present invention provides an isolated and purified nucleic acid comprising a sequence encoding a protein represented by SEQ ID NOs: 2, 3 or 4, and variants thereof. In preferred embodiments, the sequence is operably linked to a heterologous promoter. In other preferred embodiments, the sequence is contained within a vector. In other preferred embodiments, the vector is within a host cell.

In certain embodiments, the present invention provides a kit comprising a reagent for detecting (e.g., reagents sufficient for detecting) the presence or absence of a variant MR-1 polypeptide in a biological sample. In preferred embodiments, the kit further comprises instructions for using the kit for the detecting the presence or absence of a variant MR-1 polypeptide in a biological sample. In preferred embodiments, the reagent is one or more antibodies. In preferred embodiments, the variant MR-1 polypeptide contains an alanine to valine substitution at position 7 and/or 9.

In certain embodiments, the present invention provides a method for detection of a variant MR-1 polypeptide in a subject, comprising a) providing a biological sample from a subject, wherein the biological sample comprises a MR-1 polypeptide; and b) detecting the presence or absence of a variant MR-1 polypeptide in the biological sample. In preferred embodiments, the variant MR-1 polypeptide contains an alanine to valine mismatch at position 7 and/or 9. In some embodiments, the biological sample is selected from the group consisting of a blood sample, a tissue sample, a urine sample, and an amniotic fluid sample, although the present invention is not limited to these embodiments.

In preferred embodiments, the subject is selected from the group consisting of an embryo, a fetus, a newborn animal, and a young animal. In other preferred embodiments, the detecting comprises differential antibody binding. In other preferred embodiments, the detection comprises a Western blot. In yet other preferred embodiments, the detecting comprises detecting a variant MR-1 nucleic acid sequence.

In certain embodiments, the present invention provides an isolated and purified nucleic acid sequence that hybridizes under conditions of low, medium, or high stringency to a nucleic acid selected from the group consisting of SEQ ID NOs: 2, 3, and 4.

In certain embodiments, the present invention provides a vector comprising a nucleic acid sequence that hybridizes under conditions of low, medium, or high stringency to a nucleic acid selected from the group consisting of SEQ ID NOs: 2, 3, and 4.

In certain embodiments, the present invention provides a host cell comprising a vector comprising a nucleic acid sequence that hybridizes under conditions of low, medium, or high stringency to a nucleic acid selected from the group consisting of SEQ ID NOs: 2, 3, and 4. In preferred embodiments, the host cell is located in an organism, wherein the organism is a non-human animal.

In certain embodiments, the present invention provides a polypeptide encoded by a nucleic acid molecule containing a C66T mutation, wherein the polypeptide is encoded by a nucleic acid selected from the group consisting of SEQ ID NOs: 2 and variants thereof that are at least 80% identical to SEQ ID NOs: 2. In preferred embodiments, the protein is at least 90% or 95% identical to SEQ ID NO: 2.

In certain embodiments, the present invention provides a polypeptide encoded by a nucleic acid molecule containing a C72T mutation, wherein the polypeptide is encoded by a nucleic acid selected from the group consisting of SEQ ID NOs: 3 and variants thereof that are at least 80% identical to SEQ ID NOs: 3. In preferred embodiments, the protein is at least 90% or 95% identical to SEQ ID NO: 3.

BRIEF DESCRIPTION OF THE DRAWINGS

FIG. 1 shows wild type human MR-1 nucleic acid sequence (DNA) (SEQ ID NO: 1).

FIG. 2 shows a variant human MR-1 nucleic acid sequence (mRNA) (SEQ ID NO: 2).

FIG. 3 shows a variant human MR-1 nucleic acid sequence (mRNA) (SEQ ID NO: 3).

FIG. 4 shows a variant human MR-1 nucleic acid sequence (mRNA) (SEQ ID NO: 4).

FIG. 5 shows wild type human MR-1 amino acid sequence (SEQ ID NO: 5).

FIG. 6 shows a variant human MR-1 amino acid sequence (SEQ ID NO: 6).

FIG. 7 shows a variant human MR-1 amino acid sequence (SEQ ID NO: 7).

FIG. 8 shows a variant human MR-1 amino acid sequence (SEQ ID NO: 8).

DEFINITIONS

Figure 9:
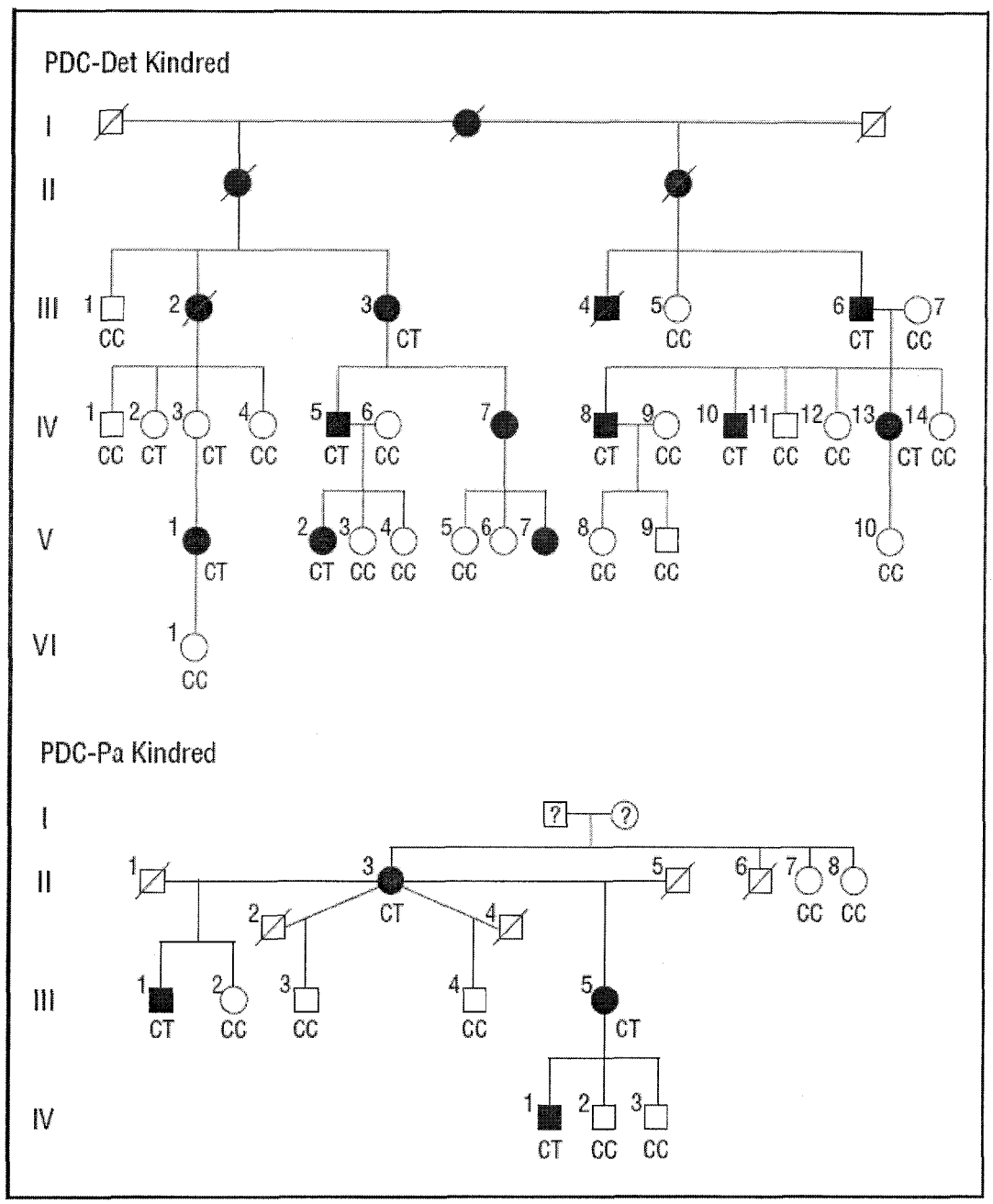
FIG. 9 shows Paroxysmal dystonic choreoathetosis (PDC) kindreds linked to the PDC locus on chromosome 2q33-2q35. Pedigrees of the PDC-Det (substitution of valine for alanine at amino acid position 9) and PDC-Pa (substitution of valine for alanine at amino acid position 7) kindreds with the myofibrillogenesis regulator 1 mutation (MR-1) are shown. Letters refer to MR-1 NM_015488 complementary DNA sequence at nucleotides 72 (PDC-Det) and 66 (PDC-Pa). Open squares indicate unaffected men; open circles, unaffected women; closed squares, affected men; closed circles, affected women; question mark, affected-unaffected status unknown; and slash, deceased.

To facilitate understanding of the invention, a number of terms are defined below.

As used herein, the term "MR-1" when used in reference to a protein or nucleic acid refers to a MR-1 protein or nucleic acid encoding a MR-1 protein of the present invention. The term MR-1 encompasses both proteins that are identical to wild-type MR-1 and those that are derived from wild type MR-1 (e.g., variants of MR-1 polypeptides of the present invention) or chimeric genes constructed with portions of MR-1 coding regions. In some embodiments, the "MR-1" is a wild type MR-1 nucleic acid (SEQ ID NO: 1) or amino acid sequence (SEQ ID NO: 5). In other embodiments, the "MR-1" is a variant or mutant nucleic acid (SEQ ID NO: 2, 3, and 4) or amino acid (SEQ ID NO: 6, 7, and 8).

As used herein, the terms "subject" and "patient" refer to any animal, such as a mammal like a dog, cat, bird, livestock, and preferably a human. Specific examples of "subjects" and "patients" include, but are not limited to, individuals with PDC, and individuals with PDC-related characteristics or symptoms.

As used herein, the terms "episodic movement disorder," "episodic neurologic disorder," "paroxysmal disorder," "paroxysmal neurological disorder," and the like, refer to neurological conditions sharing a common symptom of involuntary movements. Examples of episodic movement disorders include, but are not limited to, PDC, ataxia, bradykinesia, choreoathetosis, corticobasal degeneration, dyskinesias, dystonias, essential tremors, hereditary spastic paraplegia, Huntington's disease, multiple system atrophy, myoclonus, Parkinson's disease, progressive supranuclear palsy, restless leg syndrome, Rett syndrome, spasticity, Sydenham's chorea, tardive dyskinesia, tics, Tourette's syndrome, tremor, and Wilson's disease.

As used herein, the phrase "symptoms of PDC" and "characteristics of PDC" include, but are not limited to, attacks of involuntary movements caused by a neurological dysfunction (e.g., dystonia, chorea, athetosis) lasting up to several hours and occurring at rest both spontaneously and following caffeine or alcohol consumption.

The phrase "under conditions such that the symptoms are reduced" refers to any degree of qualitative or quantitative reduction in detectable symptoms of PDC, including but not limited to, a detectable reduction on the rate of recovery from PDC, or the reduction of at least one symptom of PDC.

The term "siRNAs" refers to short interfering RNAs. Methods for the use of siRNAs are described in U.S. Patent App. No.: 20030148519/A1 (herein incorporated by reference). In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "instructions for using said kit for said detecting the presence or absence of a variant MR-1 nucleic acid or polypeptide in said biological sample" includes instructions for using reagents contained in a kit for the detection of variant and wild type MR-1 nucleic acids or polypeptides. In some embodiments, the instructions further comprise the statement of intended use required by the U.S. Food and Drug Administration (FDA) in labeling in vitro diagnostic products.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., MR-1). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "MR-1 gene" or "MR-1 genes" refers to the full-length MR-1 nucleotide sequence (e.g., contained in SEQ ID NOs: 1, 2, 3 and 4). However, it is also intended that the term encompass fragments of the MR-1 sequences, mutants of the MR-1 sequences, as well as other domains within the full-length MR-1 nucleotide sequences. Furthermore, the terms "MR-1 nucleotide sequence" or "MR-1 polynucleotide sequence" encompasses DNA sequences, cDNA sequences, RNA (e.g., mRNA) sequences, and associated regulatory sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci. (U.S.A.)* 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., MR-1).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., a MR-1 gene of the present invention).

As used herein, the term "detection assay" refers to an assay for detecting the presence or absence of specific nucleic acid sequences (e.g., polymorphisms or mutations) in a given allele of a particular gene (e.g., a MR-1 gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. Particular examples of primers useful in the present invention include, but are not limited to, a primer of least 5 nucleotides from SEQ ID NOs: 1, 2, 3 and 4, a primer of at least 10 nucleotides from SEQ ID NOs: 1, 2, 3 and 4, a primer of at least 20 nucleotides from SEQ ID NOs: 1, 2, 3 and 4, a primer of at least 30 nucleotides in length from SEQ ID NOs: 1, 2, 3 and 4, a primer of at least 40 nucleotides in length from SEQ ID NOs: 1, 2, 3 and 4, a primer of at least 50 nucleotides in length from SEQ ID NOs: 1, 2, 3 and 4, and a primer of at least 55 nucleotides in length from SEQ ID NOs: 1, 2, 3 and 4.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding MR-1 includes, by way of example, such nucleic acid in cells ordinarily expressing MR-1 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and antisense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, MR-1 antibodies are purified by removal of contaminating non-immunoglobulin proteins; they are also purified by the removal of immunoglobulin that does not bind a MR-1 polypeptide. The removal of non-immunoglobulin proteins and/or the removal of immunoglobulins that do not bind a MR-1 polypeptide results in an increase in the percent of MR-1-reactive immunoglobulins in the sample. In another example, recombinant MR-1 polypeptides are expressed in bacterial host cells and the polypeptides are purified by the removal of host cell proteins; the percent of recombinant MR-1 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein, is used to indicate a protein that does not contain amino acid residues encoded by vector sequences; that is the native protein contains only those amino acids found in the protein as it occurs in nature. A native protein may be produced by recombinant means or may be isolated from a naturally occurring source.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced MR-1 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

A "composition comprising a given polynucleotide sequence" as used herein refers broadly to any composition containing the given polynucleotide sequence. The composition may comprise an aqueous solution. Compositions comprising polynucleotide sequences encoding MR-1s (e.g., SEQ ID NOs: 1, 2, 3 and 4) or fragments thereof may be employed as hybridization probes. In this case, the MR-1 encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

DETAILED DESCRIPTION OF THE INVENTION

The present invention relates to the MR-1 proteins and nucleic acids encoding MR-1 proteins. The present invention further provides assays for the identification of therapeutic agents, and for the detection of MR-1 polymorphisms and mutations associated with disease states. Exemplary embodiments of the present invention are described below.

Individuals with PDC are normal until they have "attacks" of involuntary movements that may last for 15 minutes to several hours. These "attacks" of involuntary movements occur spontaneously at rest without obvious provocation and also following consumption of alcohol and caffeine.

Two missense MR-1 mutations (e.g., SEQ ID NOs: 2 (C66T) and 3 (C72T) were identified within the 2q33-2q35 chromosomal locus as segregating with individuals suffering from PDC and not segregating with control individuals (as described in Examples 1-11). These mutations predict substitutions of valine for alanine at residue 9 (A9V) and residue 7 (A7V). The alanine residues at positions 7 and 9 are part of an amino-terminal cc helix that becomes disrupted with either valine substitution. The 7Ala and 9Ala residues are conserved in the 2 species (human and mouse) for which the MR-1 cDNA sequence is known and in the amino acid sequence deduced from rat genomic DNA (see, e.g., contig NW_047816).

MR-1 sequences are present in 2 transcripts, NM_015488 and NM_022573, that share 8 exons but differ in the first 2 exons. The MR-1 transcript NM_015488 (derived from 10 exons spanning 76.3 kb of genomic DNA) encodes a 385 amino acid protein of 42.9 kDa (predicted). The MR-1 transcript NM_022573 (derived from 9 exons spanning 23.5 kb of genomic DNA) encodes a 361 amino acid protein of 40.7 kDa (predicted). Only the MR-1 transcript NM_015488 contained exon 1. The MR-1 NM_015488 transcript containing exon 1 is expressed only in the brain. The PDC-specific MR-1 NM_015488 mutations C66T and C72T are present in exon 1. That this exon is expressed only in the brain could explain why PDC symptoms are restricted to this area.

Discovery of the cause of PDC a) provides laboratory-based and clinical based diagnostic testing for the disorder; b) provides methods of identifying and characterizing treatments for the disorder; c) provide insights into the causes and treatments for other episodic movement disorders including dystonias, Parkinson's disease, Tics, Tourette's syndrome, choreas including Huntington's chorea, drug-induced movement disorders including neuroleptic induced tardive dyskinesia; and d) provide insights into the neurophysiologic effects of alcohol and caffeine on the nervous system.

MR-1 gene sequence analysis can be used to diagnose PDC in an individual and distinguish this condition from other episodic and non-episodic movement disorders. Knowledge that a MR-1 pathway disturbance and/or MR-1 gene mutation results in PDC can be applied directly to genetic testing to diagnose this disease; provide genetic counseling for this disease; or to diagnose related episodic movement disorders Genetic and/or enzyme testing can indicate individual sensitivity to drug-induced movement disorders. Attacks of involuntary movements in PDC are often triggered by specific drugs (alcohol and caffeine). Drug-induced movement disorders are a common problem in medicine, particularly with the use of neuroleptic medications (including, e.g., haloperidol and thioridazine) in which the appearance of drug-induced abnormal movements ("tardive dyskinesia") may cause profound and permanent impairment. Discovery that MR-1 gene mutations cause a drug-induced movement disorder provides insight into this process for other types of drug-induced movement disorders. This information provides insight into the causes and treatments for these other types of drug-induced movement disorders.

Knowledge that genetic variation in MR-1 and the MR-1 pathway cause human neurologic disease, combined with knowledge that symptoms related to PDC are exacerbated following alcohol or caffeine consumption can be used as the basis for genetic testing to determine human and animal vulnerability to the neurotoxic effects of alcohol and caffeine or other drugs that cause involuntary movements. One application is the screening of individuals taking neuroleptic medications for risk of developing drug induced involuntary movements.

Knowledge that genetic variation in MR-1 and the MR-1 pathway cause human neurologic disease (e.g., PDC) provides therapeutic pathways (including but not limited to MR-1 protein or gene replacement) for these disorders.

Knowledge that genetic variation in the MR-1 pathway and MR-1 gene mutations cause involuntary movements can be used as the basis for treatment of episodic movement disorders (including, but not limited to, dystonias, choreas, tremor, tics, Tourette's drug-induced movement disorders, and other paroxysmal neurologic diseases including epilepsy, restless leg syndrome, migraine, episodic dystonias, episodic ataxias). Such treatments include (but are not limited to) replacement of MR-1 biochemical function either as small molecule biochemical intermediate or protein (such as enzyme) or gene replacement strategies.

The present invention is described in more detail in the following sections: I. MR-1 Polynucleotides, II. MR-1 Polypeptides, III. Detection of MR-1 Alleles IV. Generation of MR-1 Antibodies, V. Gene Therapy Using MR-1, VI. Transgenic Animals Expressing Exogenous MR-1 Genes and Homologs, Mutants, and Variants Thereof, VII. Drug Screening Using MR-1, VIII. Pharmaceutical Compositions Containing MR-1 Nucleic Acid, Peptides, and Analogs, and IX. RNAi for MR-1.

I. MR-1 Polynucleotides

As described above, the present invention provides novel MR-1 family genes. Accordingly, the present invention provides nucleic acids encoding MR-1 genes, homologs, variants (e.g., polymorphisms and mutants), including but not limited to, those described in SEQ ID NOs: 1, 2, 3 and 4. Table 1 describes exemplary MR-1 genes of the present invention. In some embodiments, the present invention provides polynucleotide sequences that are capable of hybridizing to SEQ ID NOs: 1, 2, 3 and 4 under conditions of low to high stringency as long as the polynucleotide sequence capable of hybridizing encodes a protein that retains a biological activity of the naturally occurring MR-1s. In some embodiments, the protein that retains a biological activity of naturally occurring MR-1 is 70% homologous to wild-type MR-1, preferably 80% homologous to wild-type MR-1, more preferably 90% homologous to wild-type MR-1, and most preferably 95% homologous to wild-type MR-1. In preferred embodiments, hybridization conditions are based on the melting temperature ($T_m$) of the nucleic acid binding complex and confer a defined "stringency" as explained above (See e.g., Wahl, et al., Meth. Enzymol., 152:399-407 [1987], incorporated herein by reference).

In other embodiments of the present invention, additional alleles of MR-1 genes are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids.

Each of these types of changes may occur alone, or in combination with the others, and at the rate of one or more times in a given sequence. Examples of the alleles of the present invention include that encoded by SEQ ID NO: 1 (wild type) and disease alleles thereof (e.g., SEQ ID NOs: 2, 3 and 4). Additional examples include truncation mutations (e.g., such that the encoded mRNA does not produce a complete protein). Mutations or sequences that are in linkage disequilibrium with mutations described herein may also be detected as a surrogate for detecting the mutations directly.

In still other embodiments of the present invention, the nucleotide sequences of the present invention may be engineered in order to alter an MR-1 coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of MR-1 may be extended utilizing the nucleotide sequence in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 [1993]). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T)

library does not yield full-length cDNA. Genomic mammalian libraries are useful for obtaining introns and extending 5' sequence.

In other embodiments of the present invention, variants of the disclosed MR-1 sequences are provided (e.g., SEQ ID NOs: 2, 3 and 4). In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., MR-1 function) for such purposes as altering the biological activity (e.g., altered MR-1 function). Such modified peptides are considered functional equivalents of peptides having an activity of a MR-1 peptide as defined herein. A modified peptide can be produced in which the nucleotide sequence encoding the polypeptide has been altered, such as by substitution, deletion, or addition. In particularly preferred embodiments, these modifications do not significantly reduce the biological activity of the modified MR-1 genes. In other words, construct "X" can be evaluated in order to determine whether it is a member of the genus of modified or variant MR-1's of the present invention as defined functionally, rather than structurally. In preferred embodiments, the activity of variant MR-1 polypeptides is evaluated by methods described herein (e.g., the generation of transgenic animals or the use of signaling assays).

Moreover, as described above, variant forms of MR-1 genes are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of MR-1 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine); (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a MR-1 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

TABLE 1

MR-1 Genes

| MR-1 Gene | SEQ ID NO (Nucleic acid) | SEQ ID NO (Polypeptide) |
|---|---|---|
| MR-1 | 1 | 5 |
| MR-1 (C66T) | 2 | 6 |
| MR-1 (C72T) | 3 | 7 |
| MR-1 (C66T) (C72T) | 4 | 8 |

II. MR-1 Polypeptides

In other embodiments, the present invention provides MR-1 polynucleotide sequences that encode MR-1 polypeptide sequences (e.g., the polypeptides of SEQ ID NOs: 5, 6, 7 and 8). Other embodiments of the present invention provide fragments, fusion proteins or functional equivalents of these MR-1 proteins. In some embodiments, the present invention provides mutants of MR-1 polypeptides. In still other embodiments of the present invention, nucleic acid sequences corresponding to MR-1 variants, homologs, and mutants may be used to generate recombinant DNA molecules that direct the expression of the MR-1 variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs: 1, 2, 3 and 4 that encode substantially the same or a functionally equivalent amino acid sequence, may be used to clone and express MR-1. In general, such polynucleotide sequences hybridize to SEQ ID NOs: 1, 2, 3 and 4 under conditions of high to medium stringency as described above. As will be understood by those of skill in the art, it may be advantageous to produce MR-1 encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of MR-1 expression or to produce recombinant RNA transcripts having desirable properties, such as a longer half-life, than transcripts produced from naturally occurring sequence.

1. Vectors for Production of MR-1

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1, 2, 3 and 4). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOs: 1, 2, 3 and 4) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of genes in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 by that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of MR-1 Polypeptides

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of MR-1 Polypeptides

The present invention also provides methods for recovering and purifying MR-1 polypeptides from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having a coding sequence of a MR-1 gene (e.g., SEQ ID NOs: 1, 2, 3 and 4) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of MR-1 Polypeptide

In addition, the present invention provides fragments of MR-1 polypeptides (i.e., truncation mutants). In some embodiments of the present invention, when expression of a portion of the MR-1 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing MR-1

The present invention also provides fusion proteins incorporating all or part of the MR-1 polypeptides of the present invention. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a MR-1 protein. In some embodiments of the present invention, the VP6 capsid protein of rotavirus is used as an immunologic carrier protein for portions of a MR-1 polypeptide, either in the monomeric form or in the form of a viral particle. In other embodiments of the present invention, the nucleic acid sequences corresponding to the portion of a MR-1 polypeptide against which antibodies are to be raised can be incorporated into a fusion gene construct which includes coding sequences for a late vaccinia virus structural protein to produce a set of recombinant viruses expressing fusion proteins comprising a portion of MR-1 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of a MR-1 polypeptide and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of MR-1 is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the MR-1 proteins can also be expressed and presented by bacterial cells.

In addition to utilizing fusion proteins to enhance immunogenicity, it is widely appreciated that fusion proteins can also facilitate the expression of proteins, such as a MR-1 protein of the present invention. Accordingly, in some embodiments of the present invention, MR-1 polypeptides can be generated as glutathione-S-transferase (i.e., GST fusion proteins). It is contemplated that such GST fusion proteins will enable easy purification of MR-1 polypeptides, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(H is)/enterokinase cleavage site sequence at the N-terminus of the desired portion of a MR-1 polypeptide, can allow purification of the expressed MR-1 fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of MR-1

Still other embodiments of the present invention provide mutant or variant forms of MR-1 polypeptides (i.e., muteins). It is possible to modify the structure of a peptide having an activity of a MR-1 polypeptide of the present invention for such purposes as enhancing therapeutic or prophylactic efficacy, disabling the protein, or stability (e.g., ex vivo shelf life, and/or resistance to proteolytic degradation in vivo). Such modified peptides are considered functional equivalents of peptides having an activity of the subject MR-1 proteins as defined herein. A modified peptide can be produced in which the amino acid sequence has been altered, such as by amino acid substitution, deletion, or addition.

Moreover, as described above, variant forms (e.g., mutants or polymorphic sequences) of the subject MR-1 proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present MR-1 proteins, as well as truncation mutants, and is especially useful for identifying potential variant sequences (i.e., mutants or polymorphic sequences) that are involved in episodic movement disorders (e.g., PDC) or resistance to episodic movement disorders. The purpose of screening such combinatorial libraries is to generate, for example, novel MR-1 variants that can act as either agonists or antagonists, or alternatively, possess novel activities all together.

Therefore, in some embodiments of the present invention, MR-1 variants are engineered by the present method to provide altered (e.g., increased or decreased) biological activity. In other embodiments of the present invention, combinatorially-derived variants are generated which have a selective potency relative to a naturally occurring MR-1. Such proteins, when expressed from recombinant DNA constructs, can be used in gene therapy protocols.

Still other embodiments of the present invention provide MR-1 variants that have intracellular half-lives dramatically different than the corresponding wild-type protein. For example, the altered protein can be rendered either more stable or less stable to proteolytic degradation or other cellular process that result in destruction of, or otherwise inactivate MR-1 polypeptides. Such variants, and the genes which encode them, can be utilized to alter the location of MR-1 expression by modulating the half-life of the protein. For instance, a short half-life can give rise to more transient MR-1 biological effects and, when part of an inducible expression system, can allow tighter control of MR-1 levels within the cell. As above, such proteins, and particularly their recombinant nucleic acid constructs, can be used in gene therapy protocols.

In still other embodiments of the present invention, MR-1 variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of MR-1 homologs, variants or other related proteins are aligned, preferably to promote the highest homology possible. Such a population of variants can include, for example, MR-1 homologs from one or more species, or MR-1 variants from the same species but which differ due to mutation or polymorphisms. Amino acids that appear at each position of the aligned sequences are selected to create a degenerate set of combinatorial sequences.

In a preferred embodiment of the present invention, the combinatorial MR-1 library is produced by way of a degenerate library of genes encoding a library of polypeptides which each include at least a portion of potential MR-1 protein sequences. For example, a mixture of synthetic oligonucleotides can be enzymatically ligated into gene sequences such that the degenerate set of potential MR-1 sequences are expressible as individual polypeptides, or alternatively, as a set of larger fusion proteins (e.g., for phage display) containing the set of MR-1 sequences therein.

There are many ways by which the library of potential MR-1 homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential MR-1 sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223,409, 5,198,346, and 5,096,815; each of which is incorporated herein by reference).

It is contemplated that the MR-1 nucleic acids of the present invention (e.g., SEQ ID NOs: 1, 2, 3 and 4, and fragments and variants thereof) can be utilized as starting nucleic acids for directed evolution. These techniques can be utilized to develop MR-1 variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for MR-1 activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for MR-1 activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of MR-1 homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of MR-1 Polypeptides

In an alternate embodiment of the invention, the coding sequence of MR-1 is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, *Tetrahedron Lett.,* 21:719 [1980]; and Chow and Kempe, Nucl. Acids Res., 9:2807 [1981]). In other embodiments of the present invention, the protein itself is produced using chemical methods to synthesize either an entire MR-1 amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of a MR-1 polypeptide, or any part thereof, may be altered during direct synthesis and/or combined using chemical methods with other sequences to produce a variant polypeptide.

III. Detection of MR-1 Alleles

In some embodiments, the present invention provides methods of detecting the presence of wild type or variant (e.g., mutant or polymorphic) MR-1 nucleic acids or polypeptides. The detection of mutant MR-1 polypeptides finds use in the diagnosis of disease (e.g., PDC).

A. Detection of Variant MR-1 Alleles

In some embodiments, the present invention provides alleles of MR-1 that increase a patient's susceptibility to episodic movement disorders (e.g., PDC). Any mutation that results in an altered phenotype (e.g., attacks of involuntary movements caused by a neurological dysfunction (e.g., dystonia, chorea, athetosis) lasting up to several hours and occurring at rest both spontaneously and following caffeine or alcohol consumption) is within the scope of the present invention.

Accordingly, the present invention provides methods for determining whether a patient has an increased susceptibility to a episodic movement disorder (e.g., PDC) by determining, directly or indirectly, whether the individual has a variant MR-1 allele. In other embodiments, the present invention provides methods for providing a prognosis of increased risk for episodic movement disorder (e.g., PDC) to an individual based on the presence or absence of one or more variant alleles of MR-1.

A number of methods are available for analysis of variant (e.g., mutant or polymorphic) nucleic acid or polypeptide sequences. Assays for detection variants (e.g., polymorphisms or mutations) via nucleic acid analysis fall into several categories including, but not limited to, direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following exemplary assays are useful in the present invention: directs sequencing assays, PCR assays, mutational analysis by dHPLC (e.g., available from Transgenomic, Omaha, Nebr. or Varian, Palo Alto, Calif.), fragment length polymorphism assays (e.g., RFLP or CFLP (See e.g. U.S. Pat. Nos. 5,843,654; 5,843,669; 5,719,208; and 5,888,780; each of which is herein incorporated by reference)), hybridization assays (e.g., direct detection of hybridization, detection of hybridization using DNA chip assays (See e.g., U.S. Pat. Nos. 6,045,996; 5,925,525; 5,858,659; 6,017,696; 6,068,818; 6,051,380; 6,001,311; 5,985,551; 5,474,796; PCT Publications WO 99/67641 and WO 00/39587, each of which is herein incorporated by reference), enzymatic detection of hybridization (See e.g., U.S. Pat. Nos. 5,846,717, 6,090,543; 6,001,567; 5,985,557; 5,994,069; 5,962,233; 5,538,848; 5,952,174 and 5,919,626, each of which is herein incorporated by reference)), polymorphisms detected directly or indirectly (e.g., detecting sequences (other polymorphisms) that are in linkage disequilibrium with the polymorphism to be indentified; for example, other sequences in the 2q33-2q35 locus may be used; this method is described in U.S. Pat. No. 5,612,179 (herein incorporated by reference)) and mass spectrometry assays.

In addition, assays for the detection of variant MR-1 proteins find use in the present invention (e.g., cell free translation methods, See e.g., U.S. Pat. No. 6,303,337, herein incorporated by reference) and antibody binding assays. The generation of antibodies that specifically recognize mutant versus wild type proteins are discussed below.

B. Kits for Analyzing Risk of Episodic Movement Disorders Such as PDC

The present invention also provides kits for determining whether an individual contains a wild-type or variant (e.g., mutant or polymorphic) allele or polypeptide of MR-1. In some embodiments, the kits are useful determining whether the subject is at risk of developing a episodic movement disorder (e.g., PDC). The diagnostic kits are produced in a variety of ways. In some embodiments, the kits contain at least one reagent for specifically detecting a mutant MR-1 allele or protein. In preferred embodiments, the reagent is a nucleic acid that hybridizes to nucleic acids containing the mutation and that does not bind to nucleic acids that do not contain the mutation. In other embodiments, the reagents are primers for amplifying the region of DNA containing the mutation. In still other embodiments, the reagents are antibodies that preferentially bind either the wild-type or mutant MR-1 proteins.

In some embodiments, the kit contains instructions for determining whether the subject is at risk for a episodic movement disorder (e.g, PDC). In preferred embodiments, the instructions specify that risk for developing a episodic movement disorder such as PDC is determined by detecting the presence or absence of a mutant MR-1 allele in the subject, wherein subjects having an mutant allele are at greater risk for developing the respective disease.

The presence or absence of a disease-associated mutation in a MR-1 gene can be used to make therapeutic or other medical decisions. For example, couples with a family history of episodic movement disorders such as PDC may choose to conceive a child via in vitro fertilization and pre-implantation genetic screening. In this case, fertilized embryos are screened for mutant (e.g., disease associated) alleles of a MR-1 gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a MR-1 allele known to be associated with, for example, PDC allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packaged in any suitable manner, typically with the elements in a single container or various containers as necessary along with a sheet of instructions for carrying out the test. In some embodiments, the kits also preferably include a positive control sample.

C. Bioinformatics

In some embodiments, the present invention provides methods of determining an individual's risk of developing a episodic movement disorder (e.g., PDC) based on the presence of one or more variant alleles of a MR-1 gene. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of developing episodic movement disorders such as PDC associated with a given polymorphism, as well as the sequences). In some embodiments, one of the computers stores application programs (e.g., for analyzing the results of detection assays). Results are then delivered to the user (e.g., via one of the computers or via the internet.

For example, in some embodiments, a computer-based analysis program is used to translate the raw data generated by the detection assay (e.g., the presence, absence, or amount of a given MR-1 allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant MR-1 genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing PDC) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the association of a given MR-1 allele with an episodic movement disorder such as PDC.

IV. Generation of MR-1 Antibodies

The present invention provides isolated antibodies or antibody fragments (e.g., FAB fragments). Antibodies can be generated to allow for the detection of MR-1 proteins (e.g., wild type or mutant) of the present invention. The antibodies may be prepared using various immunogens. In one embodiment, the immunogen is a human MR-1 peptide to generate antibodies that recognize human MR-1. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against a MR-1 polypeptide. For the production of antibody, various host animals can be immunized by injection with the peptide corresponding to the MR-1 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (*Bacille Calmette-Guerin*) and *Corynebacterium parvum*).

For preparation of monoclonal antibodies directed toward MR-1, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing MR-1 specific single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for a MR-1 polypeptide.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of MR-1 (e.g., for Western blotting), measuring levels thereof in appropriate biological samples, etc. The antibodies can be used to detect a MR-1 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of a human MR-1 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of MR-1 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of MR-1 or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of MR-1. Such antibodies can also be used diagnostically to measure abnormal expression of MR-1, or the aberrant formation of protein complexes, which may be indicative of a disease state.

V. Gene Therapy Using MR-1

The present invention also provides methods and compositions suitable for gene therapy to alter MR-1 expression, production, or function. As described above, the present invention provides human MR-1 genes and provides methods of obtaining MR-1 genes from other species. Thus, the methods described below are generally applicable across many species. In some embodiments, it is contemplated that the gene therapy is performed by providing a subject with a wild-type allele of a MR-1 gene (i.e., an allele that does not contain a MR-1 disease allele (e.g., free of disease causing polymorphisms or mutations)). Subjects in need of such therapy are identified by the methods described above. In some embodiments, transient or stable therapeutic nucleic acids are used (e.g., antisense oligonucleotides, siRNAs) to reduce or prevent expression of mutant proteins. Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., May 1, Beard et al., Virol., 75-81 [1990]), ovine, porcine, avian, and simian (e.g., SAV) origin.

Preferably, the adenovirus of animal origin is a canine adenovirus, more preferably a CAV2 adenovirus (e.g. Manhattan or A26/61 strain (ATCC VR-800)). Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. Nos. 4,797,368; 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VI. Transgenic Animals Expressing Exogenous MR-1 Genes and Homologs, Mutants, and Variants Thereof The present invention contemplates the generation of transgenic animals comprising an exogenous MR-1 gene or homologs, mutants, or variants thereof. In preferred embodiments, the transgenic animal displays an altered phenotype as compared to wild-type animals. In some embodiments, the altered phenotype is the overexpression of mRNA for a MR-1 gene as compared to wild-type levels of MR-1 expression. In other embodiments, the altered phenotype is the decreased expression of mRNA for an endogenous MR-1 gene as compared to wild-type levels of endogenous MR-1 expression. In some preferred embodiments, the transgenic animals comprise mutant alleles of MR-1. Methods for analyzing the presence or absence of such phenotypes include Northern blotting, mRNA protection assays, and RT-PCR. In other embodiments, the transgenic mice have a knock out mutation of a MR-1 gene. In preferred embodiments, the transgenic animals display an altered susceptibility to episodic movement disorders (e.g., PDC).

Such animals find use in research applications (e.g., identifying signaling pathways that a MR-1 protein is involved in), as well as drug screening applications (e.g., to screen for drugs that prevent or treat episodic movement disorders such as PDC). For example, in some embodiments, test compounds (e.g., a drug that is suspected of being useful to treat PDC) are administered to the transgenic animals expressing a mutant form of MR-1 and compared with control animals expressing a wild type MR-1 allele and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]).

The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which a particular domain of a MR-1 is deleted). Methods for homologous recombination are described in U.S. Pat. No. 5,614,396, incorporated herein by reference.

VII. Drug Screening Using MR-1

In some embodiments, the isolated nucleic acid and polypeptides of MR-1 genes of the present invention (e.g., SEQ ID NOS: 1, 2, 3 and 4) and related proteins and nucleic acids are used in drug screening applications for compounds that alter (e.g., enhance or inhibit) MR-1 activity and signaling. The present invention further provides methods of identifying ligands and signaling pathways of the MR-1 proteins of the present invention.

The present invention is not limited to a particular mechanism. Indeed, an understanding of the mechanism is not necessary to practice the present invention. Nonetheless, based upon the observation that 13 other episodic movement disorders are due to ion channel gene mutations (see, e.g., Ptacek L. J., Semin. Neurol., 1999, 19:363-369; herein incorporated by reference in its entirety), it is contemplated that mutations within MR-1 results in abnormal ion localization resulting in an episodic movement disorder such as PDC.

In some embodiments, the present invention provides methods of screening compounds for the ability to alter MR-1 activity mediated by natural ligands (e.g., identified using the methods described above). Such compounds find use in the treatment of disease mediated by MR-1 family members (e.g., PDC).

In some embodiments, the present invention provides methods of screening compounds for an ability to interact with mutant MR-1 nucleic acid (e.g., SEQ ID NOs: 2, 3 and 4) and/or mutant MR-1 polypeptides (e.g., SEQ ID NOs: 6, 7 and 8), while simultaneously not interacting with wild type MR-1 nucleic acid (e.g., SEQ ID NO: 1) and/or wild type MR-1 polypeptides (e.g., SEQ ID NO: 5). Such compounds find use in the treatment of episodic movement disorders facilitated by the presence of mutant forms of MR-1 nucleic acids and/or proteins.

Another technique for drug screening provides high throughput screening for compounds having suitable binding affinity to MR-1 peptides and is described in detail in WO 84/03564, incorporated herein by reference. Briefly, large numbers of different small peptide test compounds are synthesized on a solid substrate, such as plastic pins or some other surface. The peptide test compounds are then reacted with MR-1 peptides and washed. Bound MR-1 peptides are then detected by methods well known in the art.

Another technique uses MR-1 antibodies, generated as discussed above. Such antibodies are capable of specifically binding to MR-1 peptides and compete with a test compound for binding to MR-1. In this manner, the antibodies can be used to detect the presence of any peptide that shares one or more antigenic determinants of a MR-1 peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with MR-1 genes and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding MR-1 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by MR-1 in operable association with a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminescent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to a MR-1 of the present invention, have an inhibitory (or stimulatory) effect on, for example, MR-1 expression or MR-1 activity, or have a stimulatory or inhibitory effect on, for example, the expression or activity of a MR-1 substrate. Compounds thus identified can be used to modulate or replace the activity of target gene products (e.g., MR-1 genes) either directly or indirectly in a therapeutic protocol, to elaborate the biological function of the target gene product, or to identify compounds that disrupt normal target gene interactions.

Compounds, which stimulate the activity of a variant MR-1 or mimic the activity of a non-functional variant are particularly useful in the treatment of episodic movement disorders (e.g., PDC).

In one embodiment, the invention provides assays for screening candidate or test compounds that are substrates of a MR-1 protein or polypeptide or a biologically active portion thereof. In another embodiment, the invention provides assays for screening candidate or test compounds that bind to or modulate the activity of a MR-1 protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

Modulators of MR-1 expression can also be identified. For example, a cell or cell free mixture is contacted with a candidate compound and the expression of a MR-1 mRNA or protein evaluated relative to the level of expression of the MR-1 mRNA or protein in the absence of the candidate compound. When expression of the MR-1 mRNA or protein is greater in the presence of the candidate compound than in its absence, the candidate compound is identified as a stimulator of a MR-1 mRNA or protein expression. Alternatively, when expression of MR-1 mRNA or protein is less (i.e., statistically significantly less) in the presence of the candidate compound than in its absence, the candidate compound is identified as an inhibitor of MR-1 mRNA or protein expression. The level of MR-1 mRNA or protein expression can be determined by methods described herein for detecting MR-1 mRNA or protein.

A modulating agent can be identified using a cell-based or a cell free assay, and the ability of the agent to modulate the activity of a MR-1 protein can be confirmed in vivo, e.g., in an animal such as an animal model for a disease (e.g., an animal with PDC).

B. Therapeutic Agents

This invention further pertains to novel agents identified by the above-described screening assays. Accordingly, it is within the scope of this invention to further use an agent identified as described herein (e.g., a MR-1 modulating agent or mimetic, a MR-1 specific antibody, or a MR-1-binding partner) in an appropriate animal model (such as those described herein) to determine the efficacy, toxicity, side effects, or mechanism of action, of treatment with such an agent. Furthermore, as described above, novel agents identified by the above-described screening assays can be, e.g., used for treatments of episodic movement disorders (e.g., including, but not limited to, PDC). In some embodiments, the agents are MR-1 ligands or ligand analogs (e.g., identified using the drug screening methods described above).

VIII. Pharmaceutical Compositions Containing MR-1 Nucleic Acid, Peptides, and Analogs The present invention further provides pharmaceutical compositions which may comprise all or portions of MR-1 polynucleotide sequences, MR-1 polypeptides, inhibitors or antagonists of MR-1 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant MR-1 alleles (e.g., episodic movement disorders such as PDC). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, MR-1 nucleotide and MR-1 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, MR-1 polynucleotide sequences or MR-1 amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of MR-1 may be that amount that suppresses PDC related symptoms (e.g., involuntary movement). Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of MR-1, conditions indicated on the label may include treatment of condition related to episodic movement disorders such as PDC.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts MR-1 levels.

A therapeutically effective dose refers to that amount of MR-1 that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.01 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for MR-1 than for the inhibitors of MR-1. Administration to the bone marrow may necessitate delivery in a manner different from intravenous injections.

IX. RNAi for MR-1

The present invention provides RNAi for inhibiting the expression of the MR-1 polypeptide in cells for research or therapeutic applications.

A. Designing and Testing RNAi for MR-1

In order to design siRNAs for MR-1 (e.g. that target MR-1 mRNA) software design tools are available in the art. For example, Oligoengine's web page has one such design tool that finds RNAi candidates based on Elbashir's (Elbashir et al, Methods 2002; 26: 199-213, herein incorporated by reference) criteria. Other design tools may also be used, such as the Cenix Bioscience design tool offered by Ambion. In addition, there is also the Si2 silencing duplex offered by Oligoengine.

There are also RNA folding software programs available that allow one to determine if the mRNA has a tendency to fold on its own and form a "hair-pin" (which in the case of dsRNAi is not as desirable since one goal is to have the RNAi attach to the mRNA and not itself). One preferred configuration is an open configuration with three or less bonds. Generally, a positive delta G is desirable to show that it would not tend to fold on itself spontaneously.

siRNA candidate molecules that are generated can be, for example, screened in an animal model of PDC for the quantitative evaluation of MR-1 expression in vivo using similar techniques as described above.

B. Expression Cassettes

MR-1 specific siRNAs of the present invention may be synthesized chemically. Chemical synthesis can be achieved by any method known or discovered in the art. Alternatively, MR-1 specific siRNAs of the present invention may be synthesized by methods which comprise synthesis by transcription. In some embodiments, transcription is in vitro, as from a DNA template and bacteriophage RNA polymerase promoter, in other embodiments, synthesis is in vivo, as from a gene and a promoter. Separate-stranded duplex siRNA, where the two strands are synthesized separately and annealed, can also be synthesized chemically by any method known or discovered in the art. Alternatively, ds siRNA are synthesized by methods which comprise synthesis by transcription. In some embodiments, the two strands of the double-stranded region of a siRNA are expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a siRNA specific for MR-1. In some embodiments, the transcribed siRNA forms a single strand of a separate-stranded duplex (or double-stranded, or ds) siRNA of about 18 to 25 base pairs long; thus, formation of ds siRNA requires transcription of each of the two different strands of a ds siRNA. The term "gene" in the expression cassette refers to a nucleic acid sequence that comprises coding sequences necessary for the production of a siRNA. Thus, a gene includes but is not limited to coding sequences for a strand of a ds siRNA.

Generally, a DNA expression cassette comprises a chemically synthesized or recombinant DNA molecule containing at least one gene, or desired coding sequence for a single strand of a ds siRNA, and appropriate nucleic acid sequences necessary for the expression of the operably linked coding sequence, either in vitro or in vivo. Expression in vitro may include expression in transcription systems and in transcription/translation systems. Expression in vivo may include expression in a particular host cell and/or organism. Nucleic acid sequences necessary for expression in a prokaryotic cell or in a prokaryotic in vitro expression system are well known and usually include a promoter, an operator, and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand.

In any of the expression cassettes described above, the gene may encode a transcript that contains at least one cleavage site, such that when cleaved results in at least two cleavage products. Such products can include the two opposite strands of a ds siRNA. In an expression system for expression in a eukaryotic cell, the promoter may be constitutive or inducible; the promoter may also be tissue or organ specific (e.g. specific to the eye), or specific to a developmental phase. Preferably, the promoter is positioned 5' to the transcribed region. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

C. Vectors

In other aspects of the present invention, the compositions comprise a vector comprising a gene encoding an siRNA specific for MR-1 or preferably at least one expression cassette comprising a promoter and a gene which encodes a sequence necessary for the production of a siRNA specific for MR-1 (an siRNA gene). The vectors may further comprise marker genes, reporter genes, selection genes, or genes of interest, such as experimental genes. Vectors of the present invention include cloning vectors and expression vectors. Expression vectors may be used in in vitro transcription/translation systems, as well as in in vivo in a host cell. Expression vectors used in vivo in a host cell may be transfected into a host cell, either transiently, or stably. Thus, a vector may also include sites for stable integration into a host cell genome.

In some embodiments, it is useful to clone a siRNA gene downstream of a bacteriophage RNA polymerase promoter into a multicopy plasmid. A variety of transcription vectors containing bacteriophage RNA polymerase promoters (such as T7 promoters) are available. Alternatively, DNA synthesis can be used to add a bacteriophage RNA polymerase promoter upstream of a siRNA coding sequence. The cloned plasmid DNA, linearized with a restriction enzyme, can then be used as a transcription template (See for example Milligan, J F and Uhlenbeck, O C (1989) Methods in Enzymology 180: 51-64).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, mammalian expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, a gene sequence in an expression vector which is not part of an expression cassette comprising a siRNA gene (specific for MR-1) is operatively linked to an appropriate expression control sequence(s) (promoter) to direct mRNA synthesis. In some embodiments, the gene sequence is a marker gene or a selection gene. Promoters useful in the present invention include, but are not limited to, the cytomegalovirus (CMV) immediate early, herpes simplex virus (HSV) thymidine kinase, and mouse metallothionein promoters and other promoters known to control expression of gene in mammalian cells or their viruses. In other embodiments of the present invention, recombinant expression vectors include origins of replication and selectable markers permitting transformation of the host cell (e.g., dihydrofolate reductase or neomycin resistance for eukaryotic cell culture).

In some embodiments of the present invention, transcription of DNA encoding a gene is increased by inserting an enhancer sequence into the vector. Enhancers are cis-acting elements of DNA, usually about from 10 to 300 by that act on a promoter to increase its transcription. Enhancers useful in the present invention include, but are not limited to, a cytomegalovirus early promoter enhancer, the polyoma enhancer on the late side of the replication origin, and adenovirus enhancers.

Preferably the design of a vector is configured to deliver the RNAi for more permanent inhibition. For example the pSilencer siRNA expression vector offered by Ambion, the pSuper RNAi system offered by Oligoengine, and the GneSilencer System offered by IMGENEX. These are all plasmid vector based RNAis. BD Biosciences offer the RNAi-Ready pSIREN Vectors, that allow both a Plasmid-based vectors and an Adenoviral or a Retroviral delivery formats. Ambion is expected to release an adenoviral vector for siRNA shortly. For the design of a vector there is no limitation regarding the folding pattern since there is no concern regarding the formation of a hairpin or at least there are no studies that found any difference in performance related to the mRNA folding pattern.

It is noted that Ambion offers a design tool for a vector on their web page, and BD Biosciences offers a manual for the design of a vector, both of which are useful for designing vectors for siRNA.

D. Transfecting Cells

In yet other aspects, the present invention provides compositions comprising cells transfected by an expression cassette of the present invention as described above, or by a vector of the present invention, where the vector comprises an expression cassette (or simply the siRNA gene) of the present invention, as described above. In some embodiments of the present invention, the host cell is a mammalian cell. A transfected cell may be a cultured cell or a tissue, organ, or organismal cell. Specific examples of cultured host cells include, but are not limited to, Chinese hamster ovary (CHO) cells, COS-7 lines of monkey kidney fibroblasts, 293T, C127, 3T3, HeLa, and BHK cell lines. Specific examples of host cells in vivo include tumor tissue and eye tissue.

The cells may be transfected transiently or stably (e.g. DNA expressing the siRNA is stably integrated and expressed by the host cell's genome). The cells may also be transfected with an expression cassette of the present invention, or they are transfected with an expression vector of the present invention. In some embodiments, transfected cells are cultured mammalian cells, preferably human cells. In other embodiments, they are tissue, organ, or organismal cells.

In the present invention, cells to be transfected in vitro are typically cultured prior to transfection according to methods which are well known in the art, as for example by the preferred methods as defined by the American Tissue Culture Collection. In certain embodiments of the present invention, cells are transfected with siRNAs that are synthesized exogenously (or in vitro, as by chemical methods or in vitro transcription methods), or they are transfected with expression cassettes or vectors, which express siRNAs within the transfected cell.

In some embodiments, cells are transfected with siRNAs by any method known or discovered in the art which allows a cell to take up exogenous RNA and remain viable. Non-limiting examples include electroporation, microinjection, transduction, cell fusion, DEAE dextran, calcium phosphate precipitation, use of a gene gun, osmotic shock, temperature shock, and electroporation, and pressure treatment. In alternative, embodiments, the siRNAs are introduced in vivo by lipofection, as has been reported (as, for example, by Elbashir et al. (2001) Nature 411: 494-498, herein incorporated by reference).

In other embodiments expression cassettes or vectors comprising at least one expression cassette are introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267: 963; Wu and Wu (1988) J. Biol. Chem., 263:14621; and Williams et al. (1991) Proc. Natl. Acad. Sci. USA 88:272). Receptor-mediated DNA delivery approaches are also used (Curiel et al. (1992) Hum. Gene Ther., 3:147; and Wu and Wu (1987) J. Biol. Chem., 262:4429). In some embodiments, various methods are used to enhance transfection of the cells. These methods include but are not limited to osmotic shock, temperature shock, and electroporation, and pressure treatment.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes. Particularly useful lipid compounds and compositions for transfer of nucleic acids are described in WO95/18863 and WO96/17823, and in U.S. Pat. No. 5,459,127, herein incorporated by reference. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a sequence encoding a siRNA in vivo as a naked DNA, either as an expression cassette or as a vector. Methods for formulating and administering naked DNA to mammalian muscle tissue are disclosed in U.S. Pat. Nos. 5,580,859 and 5,589,466, both of which are herein incorporated by reference.

Stable transfection typically requires the presence of a selectable marker in the vector used for transfection. Transfected cells are then subjected to a selection procedure. Generally, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

In preferred embodiments, the transfecting agent is OLIGOFECTAMINE. OLIGOFECTAMINE is a lipid based transfection reagent. Additional example of lipid based transfection reagents that were designed for the transfection of dsRNAis are the Transit-TKO reagent which is provided by Mirus (Madison, Wis.) and the jetSI which was introduced by Polyplus-transfection SAS. In addition, the Silencer siRNA Transfection Kit provided by Ambion's includes siPORT Amine and siPORT Lipid transfection agents. Roche offers the Fugene 6 transfection reagents that are also lipid based. There is an option to use electroporation in cell culture. Preferably a plasmid vector delivery system is transfected into the cell with OLIGOFECTAMINE provided by Invitrogen or with siPORT XP-1 transfection agent provided by Ambion.

In certain embodiments, certain chemical modifications of the dsRNAis such as changing the lipophilicity of the molecule may be employed (e.g., attachment of lipophilic residues at the 3' termini of the dsRNA). Delivery of dsRNAs into organisms may also be achieved with methods previously developed for the application of antisense oligonucleotides such as injection of liposomes-encapsulated molecules.

E. Kits

The present invention also provides kits comprising at least one expression cassette comprising a siRNA gene specific for MR-1 or a variant of MR-1. In some aspects, a transcript from the expression cassette forms a double stranded siRNA of about 18 to 25 base pairs long. In other embodiments, the expression cassette is contained within a vector, as described above, where the vector can be used in in vitro transcription or transcription/translation systems, or used in vivo to transfect cells, either transiently or stably.

In other aspects, the kit comprises at least two expression cassettes, each of which comprises a siRNA gene, such that at least one gene encodes one strand of a siRNA that combines with a strand encoded by a second cassette to form a ds siRNA; the ds siRNA so produced is any of the embodiments described above. These cassettes may comprise a promoter and a sequence encoding one strand of a ds siRNA. In some further embodiments, the two expression cassettes are present in a single vector; in other embodiments, the two expression cassettes are present in two different vectors. A vector with at least one expression cassette, or two different vectors, each comprising a single expression cassette, can be used in in vitro transcription or transcription/translation systems, or used in vivo to transfect cells, either transiently or stably.

In yet other aspects, the kit comprises at least one expression cassettes which comprises a gene which encodes two separate strands of a ds siRNA and a processing site between the sequences encoding each strand such that, when the gene is transcribed, the transcript is processed, such as by cleavage, to result in two separate strands which can combine to form a ds siRNA, as described above.

In some embodiments, the present invention provides kits comprising: a) a composition comprising small interfering RNA duplexes (siRNAs) configured to inhibit expression of an MR-1 protein, and/or b) printed material with instructions for employing the composition for treating a target cell expressing MR-1 protein via expression of MR-1 mRNA under conditions such that the MR-1 mRNA is cleaved or otherwise disabled. In certain embodiments, the printed material comprises instructions for employing the composition for treating eye disease.

F. Generating MR-1 Specific siRNA

The present invention also provides methods of synthesizing siRNAs specific for MR-1 (e.g. human MR-1) or specific for mutant or wild type forms of MR-1. The siRNAs may be synthesized in vitro or in vivo. In vitro synthesis includes chemical synthesis and synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The siRNAs synthesized in vitro, either chemically or by transcription, are used to transfect cells. Therefore, the present invention also provides methods of transfecting host cells with siRNAs synthesized in vitro; in particular embodiments, the siRNAs are synthesized by in vitro transcription. The present invention further provides methods of silencing the MR-1 gene in vivo by transfecting cells with siRNAs synthesized in vitro. In other methods, the siRNAs is expressed in vitro in a transcription/translation system from an expression cassette or expression vector, along with an expression vector encoding and expressing a reporter gene.

The present invention also provides methods of expressing siRNAs in vivo by transfecting cells with expression cassettes or vectors which direct synthesis of siRNAs in vivo. The present invention also provides methods of silencing genes in vivo by transfecting cells with expression cassettes or vectors that direct synthesis of siRNAs in vivo.

EXAMPLES

The following examples are provided in order to demonstrate and further illustrate certain preferred embodiments and aspects of the present invention and are not to be construed as limiting the scope thereof.

Example 1

This example describes the subjects used in experiments conducted during the course of the present invention. Subjects participated according to the University of Michigan (Ann Arbor) institutional reviewboard-approved protocol. Subjects were diagnosed as either affected with PDC or unaffected prior to genetic linkage and candidate gene analysis. Diagnosis was based on normal developmental milestones, observed descriptions of episodes consistent with nonkinesigenic, nonhypnogenic paroxysmal dyskinesia lasting longer than 5 minutes, normal interictal neurologic examination results, and witnessed episodes that were consistent with PDC. Control subjects were older than 60 years and were determined by neurological examination and structured psychiatric interview to have no personal or family history of neurologic or psychiatric disorders.

Example 2

This example describes the performed genetic linkage analysis. DNA was extracted from peripheral blood leukocytes, microsatellite DNA polymorphisms, and 2-point lod scores calculated as previously described (see, e.g., Rainier S., et al., Am J Hum Genet. 2003, 73:967-971; Zhao X., et al., Nat. Genet. 2001, 29:326-331; each herein incorporated by reference in their entireties). Genetic linkage analysis of the PDC-Det kindred (substitution of valine for alanine at amino acid position 9) (see FIG. 9) was reported previously (see, e.g., Fink J. K., et al., Am J Hum Genet. 1996, 59:140-145; herein incorporated by reference in its entirety). For the PDC-Pa kindred (substitution of valine for alanine at amino acid position 7) (see, e.g., FIG. 9), genetic linkage between the disorder and the PDC locus was assessed by the examination of markers D2S295, D2S2210, D2S434, D2S2249, D2S94, D2S173, D2S2179, D2S104, D2S2250, D2S433, D2S2244, D2S2151, and D2S163 using an autosomal dominant mode of inheritance, applying an assumed disease allele frequency of 0.001, and assigning genetic penetrance to 0.90. Allele frequencies were assumed to be equal because there were too few marrying-in spouses to calculate allele frequencies accurately.

Example 3

This example describes the physical mapping of the PDC locus interval. A physical map across the consensus PDC locus interval (D2S295-D2S163) consisting of 22 overlapping bacterial artificial chromosome elements was created. Subsequently, the Human Genome Project created overlapping contigs (NT_005337 and NT_005289, that were combined into contig NT_005403 that included the 2.4-Mb PDC locus and for which DNA sequences were made publicly available. It was confirmed that the sequence tagged site (STS) content of these contigs by a combination of STS amplification from individual bacterial artificial chromosome elements and Basic Local Alignment Search Tool analysis to determine if the DNA sequences of given STSs were contained in the annotated contig sequence.

Example 4

This example describes the identification, prioritization and analysis of the PDC candidate genes. 116 potential candidate genes were identified in the PDC contig by analysis of expressed sequence tags and complementary DNA (cDNA) sequences listed with annotated contigs from the National Center for Biotechnology Information (Bethesda, Md.) and by Pipeline analysis of contig and individual bacterial artificial chromosome DNA sequences. Involuntary movements in PDC involve (but do not necessarily originate in) the extrapyramidal motor system. Therefore, to prioritize the analysis of 116 positional candidate genes, reverse transcription-polymerase chain reaction (RT-PCR) was used to determine which candidate genes were expressed in the brain. For this, a Superscript RT-PCR kit (Invitrogen, Carlsbad, Calif.) was used to amplify candidate genes from adult brain messenger RNA (mRNA) (Stratagene, La Jolla, Calif.). Whenever possible, exonic primers were used to amplify across small introns so that it could be determined by amplification fragment size whether the template consisted of cDNA or contaminating genomic DNA. When intronic sequences were less than 3 kilobases (kb), RT-PCR amplification products was compared with those obtained from the genomic DNA template.

Example 5

This example describes an analysis of MR-1 gene expression in multiple tissues by RT-PCR. This analysis was performed using a Superscript RT-PCR kit (Invitrogen) to amplify a fragment of the MR-1 gene from the adult brain, liver, kidney, skeletal muscle, heart, and lung mRNA (Stratagene). Placement of the forward primer (5_-ATCTGAACATGGCGGCGGTGGTAG-3_) (SEQ ID NO: 9) in MR-1 NM_015488 exon 1 and the reverse primer (5_-AGTGGCCTTTAGGGTAGCGATTCC-3_) (SEQ ID NO: 10) in MR-1 NM_015488 exon 3 resulted in a 333-base pair (bp) cDNA amplification product. Inclusion of introns 1 and 2 allowed size discrimination of amplification products from mRNA (333 bp) and genomic DNA templates (_50 kb). The RT-PCR amplification of a 626-bp β-actin mRNA fragment served as a control and was performed with previously described primers and methods (see, e.g., Raff T., et al., Biotechniques 1997, 23:456-460; herein incorporated by reference in its entirety). The conditions were the same for both MR-1 and β-actin amplification (50° C. for 30 minutes, denaturation for 2 minutes at 94° C., followed by 34 cycles each at 94° C. for 15 seconds, 55° C. for 30 seconds, and 72° C. for 1 minute, followed by 10-minute elongation at 72° C.).

Example 6

This example describes protein sequence analysis. The MR-1 homologues were found using Tblastn, the protein query of the translated database. The secondary structure prediction was performed using Protean sequence analysis software (DNASTAR, Madison, Wis.).

Example 7

This example describes the clinical features of the subjects. Clinical features and (+)-α-[11C]dihydrotetrabenazine positron emission tomography for the PDC-Det kindred have previously been reported (see, e.g., Fink J. K., et al., Neurology. 1997, 49:177-183; Bohnen N. I., et al., Neurology. 1999, 52:1067-1069; each herein incorporated by reference in their entireties). The PDC-Det kindred was of Polish ancestry, and the PDC-Pa kindred was of English and mixed European ancestry. The clinical syndrome of early childhood-onset nonkinesigenic dyskinesia in affected subjects in the PDC-Pa family was very similar to that previously described for the PDC-Det family (see, e.g., Fink J. K., et al., Neurology. 1997, 49:177-183; herein incorporated by reference in its entirety). Affected subjects in the PDC-Pa kindred experienced episodes (ranging from once a week to several times a day) of involuntary movements involving the face and all extremities that lasted from 5 minutes to more than 1 hour. Episodes occurred spontaneously while at rest and following caffeine or alcohol consumption. These involuntary movements did not occur during sleep, when falling asleep, or when waking up and were not provoked by exercise or sudden movement. Developmental milestone and interictal neurologic examination results were normal in all subjects with the exception of 1 individual who had childhoodonset polio and 1 subject who had facial tics (blinking), both of whom were in the PDC-Det kindred and have been described previously (see, e.g., Fink J. K., et al., Neurology. 1997, 49:177-183; herein incorporated by reference in its entirety).

Example 8

This example describes the linkage of the disorder in PDC-DET and PDC-PA kindreds to Chromosome 2q33-2q35. Linkage of this disorder to chromosome 2q33-2q35 in the PDC-Det kindred (maximum 2-point lod score, +4.77 at θ=0 for marker D2S173 [AFM249wg9]) has been reported (see, e.g., Fink J. K., Am J Hum Genet. 1996, 59:140-145; herein incorporated by reference in its entirety). Analysis of the PDC-Pa kindred (FIG. 9) was also consistent with linkage to this locus (maximum 2-point lod score, +2.41 at _=0 for D2S163).

Example 9

This example describes haplotype analysis. Extended haplotypes for linked markers in PDC-Det and PDC-Pa families was analyzed and no evidence of haplotype sharing was found. Therefore, there was no evidence that these 2 families were closely related.

Example 10

This example describes the identification and analysis of PDC positional candidate genes. RT-PCR analysis provided evidence that 45 of the 116 known and putative genes in the PDC locus interval were transcribed in the brain. Intron-exon boundaries were identified, and candidate gene sequencing was performed as previously described (see, e.g., Rainier S., et al., Am J Hum Genet. 2003, 73:967-971; Zhao X., et al., Nat. Genet. 2001; 29:326-331; each herein incorporated by reference in their entireties). Analysis of 17 of these genes did not disclose PDC-specific, nonconserved coding sequence mutations (see, e.g., Grunder S., et al., Eur J Hum Genet. 2001, 9:672-676; Tokarz D., et al., Am J Hum Genet. 2001; 69:629; each herein incorporated by reference in their entireties).

Example 11

Figure 10:
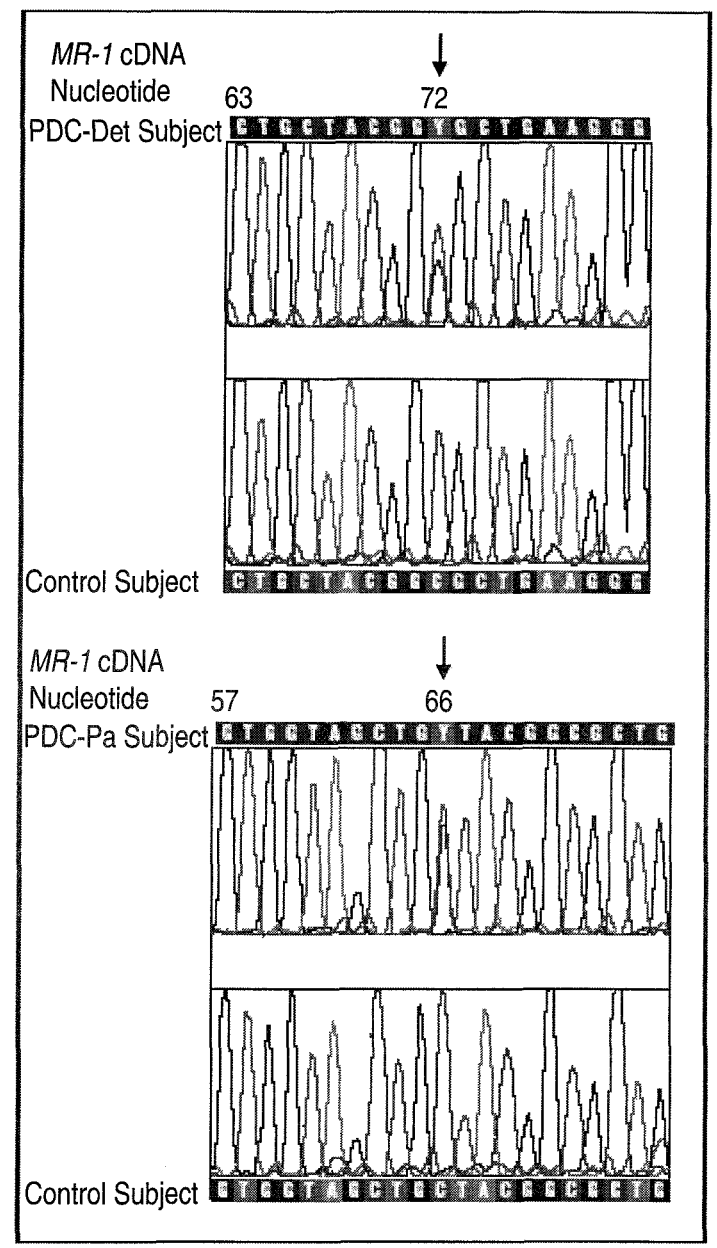
FIG. 10 (SEQ ID NOS: 11-14) shows myofibrillogenesis regulator 1 mutations (MR-1) in subjects with paroxysmal dystonic choreoathetosis (PDC). Representative MR-1 sequence of normal and affected subjects from PDC-Det (substitution of valine for alanine at amino acid position 9) and PDC-Pa (substitution of valine for alanine at amino acid position 7) kindreds are shown. The arrows mark the position of the MR-1 NM_015488 mutation in the PDC-Det (complementary DNA [cDNA] nucleotide C72T) and PDC-Pa (cDNA nucleotide C66T) kindreds.

This example describes the identification and analysis of MR-1 gene mutations in subjects with PDC. The MR-1 gene was identified as a positional candidate gene of unknown function and was expressed in the brain. The National Center for Biotechnology Information database lists 2 MR-1 transcripts (NM_015488 and NM_022572). These transcripts have identical sequences for their last 8 exons but differ in their first 2 exons. NM_015488 is the larger transcript (3032 bp) and encodes a 385 amino acid protein with a predicted molecular weight of 42.9 kDa. NM_022572 is a slightly smaller transcript (2918 bp) that encodes a 361amino acid protein with a predicted molecular weight of 40.7 kDa. Exons 1 and 2 (284 bp combined) of the larger transcript contain 47 by of a 5_untranslated sequence and encode 79amino acids that are not present in the smaller MR-1 transcript. Conversely, exon 1 (165 bp) of the smaller transcript encodes 55 amino acids that are absent in the larger MR-1 transcript (GenBank accession numbers: NM_015488 and NM_022572 for human MR-1 splice variants, AY299972 for mouse MR-1, and NT_005403 for the contig containing the MR-1 gene). Each MR-1 exon (from NM_015488 and NM_022572) in affected and unaffected subjects was sequenced from the PDC-Det and PDC-Pa kindreds (see FIG. 9). Sequencing MR-1NM_015488 exon 1 in samples from the PDCDet kindred revealed heterozygosity (both C and T) at MR-1 NM_015488 cDNA nucleotide 72 in each affected subject (n=8) (FIG. 9). With the exception of 2 previously identified nonpenetrant subjects discussed as follows, each unaffected subject (n=17) and each control subject (n=105) had only C at this position, which agreed with the DNA sequence of contig NT_005289 and the MR-1 gene's published cDNA sequence (NM_015488). Sequencing MR-1 NM 015488 exon 1 in samples from the PDC-Pa kindred revealed heterozygosity (C and T) (FIG. 9) at MR-1 NM_015488 cDNA nucleotide 66 (FIG. 9 and FIG. 10) in each affected subject (n=4). This mutation was absent in unaffected relatives (n=7) and control subjects (n=105). Sequencing each remainingMR-1 NM_015488 exon and each MR-1 NM_022572 exon in 2 affected subjects from the PDC-Det and PDC-Pa kindreds revealed no other mutation.

Previously, it was reported that unaffected subject PDCDet W-2 (FIG. 9) contained the affected haplotype for PDC locus markers.7 The MR-1 NM_015488 exon 1 sequence analysis confirmed that this unaffected individual also had the C-to-T substitution at MR-1 nucleotide 72. She is thus a nonpenetrant individual as is her unaffected sibling (subject PDC-Det IV-3) (FIG. 9), who along with her affected child has the substitution of T for C at MR-1 nucleotide 72.

Figure 11:
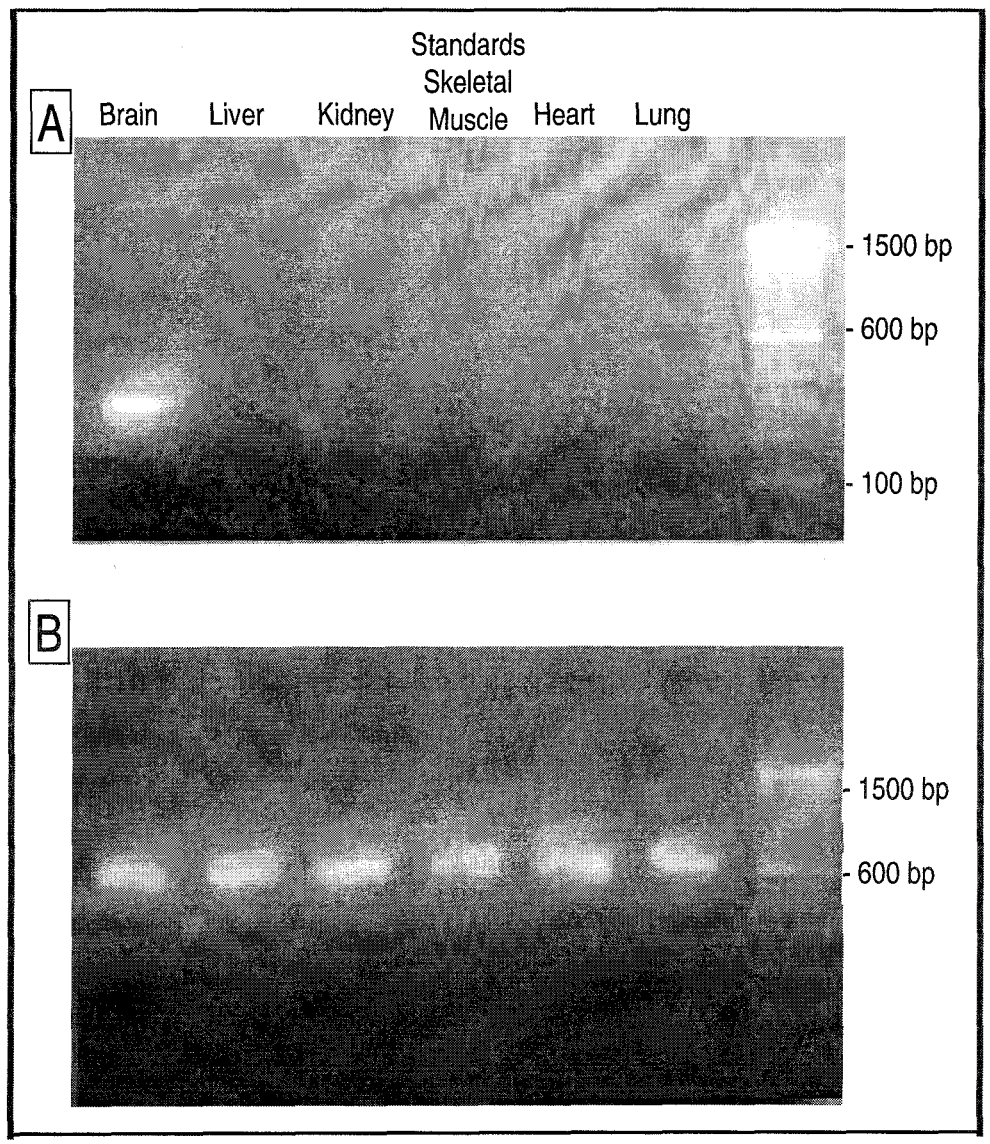
FIG. 11 shows brain-specific expression of myofibrillogenesis regulator 1 gene (MR-1) exon 1. A) Reverse transcription-polymerase chain reaction (RT-PCR) was used to amplify nucleotides 39 to 371 (333-base pair [bp] fragment) of the MR-1 NM_015488 transcript from the human adult brain, liver, kidney, skeletal muscle, heart, and lung messenger RNA (mRNA). B) The RT-PCR amplification of β-actin mRNA nucleotides 25 to 650 (626-bp fragment) from the mRNA of these tissues.

The MR-1 NM_015488 exon 1, the exon containing the C66T and C72T mutations is found only in 1 MR-1 transcript variant of NM_015488. Primers specific for this exon were created to examine MR-1 gene expression by RT-PCR. These experiments detected the expression of MR-1 NM_015488 exon 1 only in the brain (FIG. 11). MR-1 NM_015488 exon 1 was not detected in the liver, kidney, skeletal muscle, heart, or lung (FIG. 11).

Figure 12:
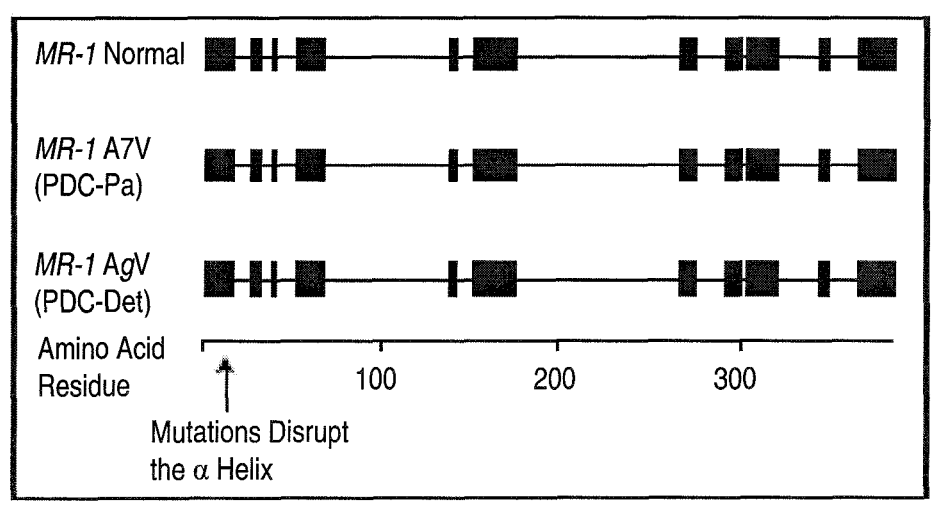
FIG. 12 shows disease-specific myofibrillogenesis regulator 1 mutations (MR-1) A7V and A9V alter predicted cc helix content of the MR-1 amino-terminal region in paroxysmal dystonic choreoathetosis (PDC) kindreds PDC-Det (substitution of valine for alanine at amino acid position 9) and PDC-Pa (substitution of valine for alanine at amino acid position 7).

Mutations at C66T and C72T predict substitutions of valine for alanine at residue 9 (A9V) and residue 7 (A7V). The alanine residues at positions 7 and 9 are part of an amino-terminal αhelix that becomes disrupted with either valine substitution (FIG. 12).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for determining a human subject's risk for paroxysmal dystonic choreoathetosis comprising providing a sample from a human subject and detecting the presence of one or more human myofibrillogenesis regulator 1 (MR-1) gene sequence variations in the coding sequence of exon 1 of the MR-1 gene in the subject sample, wherein the wild type human MR-1 gene comprises SEQ ID NO: 1, wherein the MR-1 gene sequence variations are selected from the group consisting of a C to T change at position 66 of SEQ ID NO: 1 and a C to T change at position 72 of SEQ ID NO: 1 wherein said detecting occurs with a nucleic acid sequencing assay and wherein the presence of said MR-1 gene sequence variation indicates an increased risk for paroxysmal dystonic choreoathetosis.

2. The method of claim 1, wherein said nucleic acid sequencing assay is selected from the group consisting of a direct sequencing assay, a fragment polymorphism assay, and a hybridization assay.

3. The method of claim 1, wherein said sample is selected from a blood sample, a tissue sample, a urine sample, and an amniotic fluid sample.

* * * * *

UNITED STATES PATENT AND TRADEMARK OFFICE
CERTIFICATE OF CORRECTION

| | | |
|---|---|---|
| PATENT NO. | : 8,481,260 B2 | |
| APPLICATION NO. | : 12/729773 | |
| DATED | : July 9, 2013 | |
| INVENTOR(S) | : John F. Fink and Shirley Rainier | |

It is certified that error appears in the above-identified patent and that said Letters Patent is hereby corrected as shown below:

In the Specifications

In Column 1, lines 12-14, the STATEMENT REGARDING FEDERALLY SPONSORED RESEARCH OR DEVELOPMENT section should read:

--This invention was made with government support under NS045163 awarded by the National Institutes of Health. The Government has certain rights in the invention.--

Signed and Sealed this
Twentieth Day of August, 2013

Teresa Stanek Rea
*Acting Director of the United States Patent and Trademark Office*